United States Patent [19]

Henrick

[11] Patent Number: 5,037,991

[45] Date of Patent: Aug. 6, 1991

[54] NOVEL SUBSTITUTED AROMATIC COMPOUNDS

[75] Inventor: Clive A. Henrick, Palo Alto, Calif.

[73] Assignee: Sandoz Ltd., Basel, Switzerland

[21] Appl. No.: 593,524

[22] Filed: Oct. 3, 1990

Related U.S. Application Data

[60] Continuation of Ser. No. 311,324, Feb. 14, 1989, abandoned, which is a continuation of Ser. No. 54,464, May 26, 1987, abandoned, which is a division of Ser. No. 745,105, Jun. 17, 1985, abandoned, which is a continuation-in-part of Ser. No. 631,959, Jul. 18, 1984, abandoned.

[51] Int. Cl.$^5$ ............... C07C 333/04; C07C 271/12; C07C 271/14
[52] U.S. Cl. ................... 558/234; 558/236; 558/239; 560/161; 560/164; 560/165
[58] Field of Search ................ 558/234, 236, 239; 560/161, 164, 165

[56] References Cited

U.S. PATENT DOCUMENTS

| | | | |
|---|---|---|---|
| 2,756,249 | 7/1956 | Kirchenbaum et al. | 558/236 |
| 3,277,142 | 10/1966 | Zerbe et al. | 558/239 X |
| 3,284,184 | 11/1966 | Zerbe et al. | 558/234 X |
| 3,439,021 | 4/1969 | Fancher | 560/164 |
| 3,663,709 | 5/1972 | D'Amico et al. | 558/236 X |
| 4,060,629 | 11/1977 | Karrer | 558/234 X |
| 4,066,681 | 1/1978 | Wachter | 558/234 X |
| 4,080,470 | 3/1978 | Kairer | 560/164 X |
| 4,101,670 | 7/1978 | Fujimori et al. | 558/239 X |
| 4,215,139 | 7/1980 | Fischer | 560/9 X |
| 4,451,474 | 5/1984 | Berger et al. | 546/322 X |
| 4,697,033 | 9/1987 | Henrick | 558/236 X |
| 4,713,200 | 12/1987 | Blade | 260/408 |

FOREIGN PATENT DOCUMENTS

| | | | |
|---|---|---|---|
| 88211/82 | 2/1983 | Australia . | |
| 40750/85 | 10/1985 | Australia . | |
| 2150956 | 4/1973 | Fed. Rep. of Germany . | |
| 1584844 | 1/1970 | France . | |
| 0111022 | 9/1978 | Japan | 558/239 |
| 189874 | 3/1967 | U.S.S.R. | 558/236 |
| 1259472 | 1/1972 | United Kingdom . | |
| 1382204 | 1/1975 | United Kingdom . | |

Primary Examiner—Joseph Paul Brust
Attorney, Agent, or Firm—Allen E. Norris

[57] ABSTRACT

Substituted phenoxy, phenylthio and anilino compounds, intermediates therefor, synthesis thereof, and their use for the control of pests.

13 Claims, No Drawings

NOVEL SUBSTITUTED AROMATIC COMPOUNDS

This is a continuation of Ser. No. 07/311,324 filed on Feb. 14, 1989, now abandoned, which is a continuation of Ser. No. 07/054,464 filed on May 6, 1987, now abandoned, which is a divisional of Ser. No. 06/745,105 filed on June 17, 1985, now abandoned, which is a continuation-in-part of Ser. No. 631,959 filed on July 18, 1984, now abandoned.

This invention relates to novel substituted phenoxy, phenylthio and anilino compounds of the following formula (A):

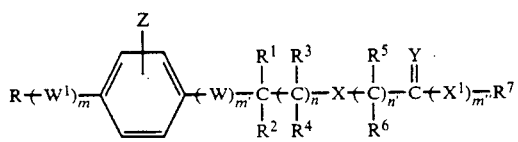

wherein,
each of m, m' and m" is independently zero or one;
n is zero, one, two or three;
n' is zero, one or two;
R is hydrogen, lower alkyl, lower alkenyl, lower alkynyl, lower haloalkyl, lower haloalkenyl, lower haloalkynyl, lower alkoxyalkyl, lower alkylthioalkyl, cycloalkyl, halocycloalky, cycloalkylalkyl, heterocycloalkyl, or heterocycloalkylalkyl;
each of $R^1$, $R^2$, $R^3$, $R^4$, $R^5$, $R^6$ and $R^8$ is independently hydrogen or lower alkyl;
$R^7$ is lower alkyl, lower alkenyl, lower alkynyl, lower haloalkyl, lower haloalkenyl, lower haloalkynyl, cycloalkyl, cycloalkylalkyl, phenyl or substituted phenyl; provided that when $X^1$ is $NR^9$, $R^7$ can also be selected from substituted or unsubstituted phenylthio and the group $S-C(CH_3)_2-CN$;
$R^9$ is hydrogen or selected from the values of $R^7$;
W is oxygen, sulfur, $NR^9$, $CR^3R^4$ or carbonyl;
$W^1$ is oxygen, sulfur, $NR^8$, $CR^3RR^4$, carbonyl, sulfinyl or sulfonyl;
X is oxygen, sulfur or $NR^8$;
$X^1$ is oxygen, sulfur or $NR^9$;
Y is oxygen, sulfur or $NR^8$; and
Z is hydrogen, lower alkyl, lower haloalkyl or halogen.

The present invention also encompasses the use of the compounds of formula (A) for the control of pest, and in particular for the control of insects.

In the description hereinafter and the claims, each of m, m', m", n, n', $R-R^9$, W, $W^1$, X, $X^1$, Y and Z is as defined above, unless otherwise specified.

The compounds of the present invention of formula (A) can be prepared by methods known in the art, such as those described in U.S. Pat. Nos. 4,080,470 and 4,215,139 and European Patent 98,800 for example, and as outlined below;

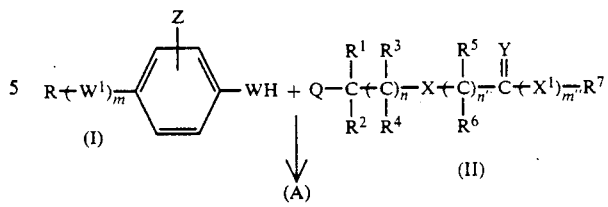

In the above synthesis, a phenol phenylthiol or aniline of formula I is reacted with a halide of formula II (Q is chlorine, bromine, or iodine) in an organic solvent such as N-methylpyrrolidone, dimethylformamide or tetrahydrofuran and at a reaction temperature of between 0° and 140°, preferably at between 10° and 110°, in the presence of a base such as potassium carbonate or sodium hydroxide. Alternatively, the salt of (I) is prepared with sodium hydride and this salt is reacted with a halide of formula II.

Alternatively, a phenol, phenylthiol or aniline of formula III is reacted with sodium hydride to form the salt and this salt is then reacted with a halide or a mesylate $R-Q^1$ (where $Q^1$ is halogen or mesyl), in an organic solvent and at room temperature or above to give a compound of formula A.

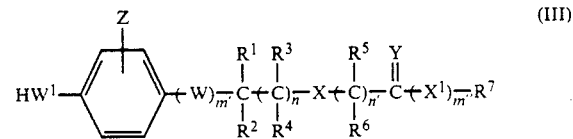

In a third synthetic method, an alcohol, thiol or amine (IV), or a salt thereof, is reacted with a halide (V) following the same general parameters and conditions as described above.

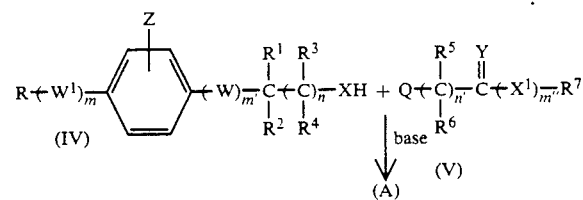

When n' is zero, m" is one, $X^1$ is NH and Y' is oxygen or sulfur, the compounds of the present invention can be prepared from an alcohol, thiol or amine (IV) and in isocyanate or isothiocyanate (VI).

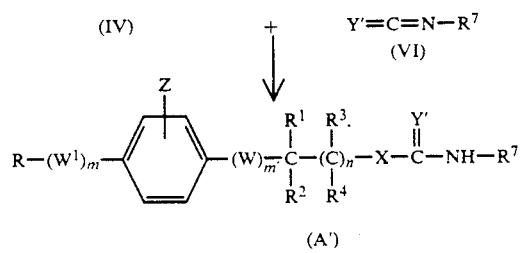

In another synthetic method, a halide of formula (VII) is reacted with an alcohol, thiol or amine (VIII), following the above procedures.

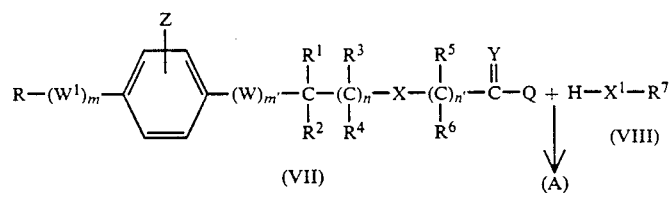

Where m' is one, W is carbonyl and X is NH, the compounds of the present invention are prepared as follows:

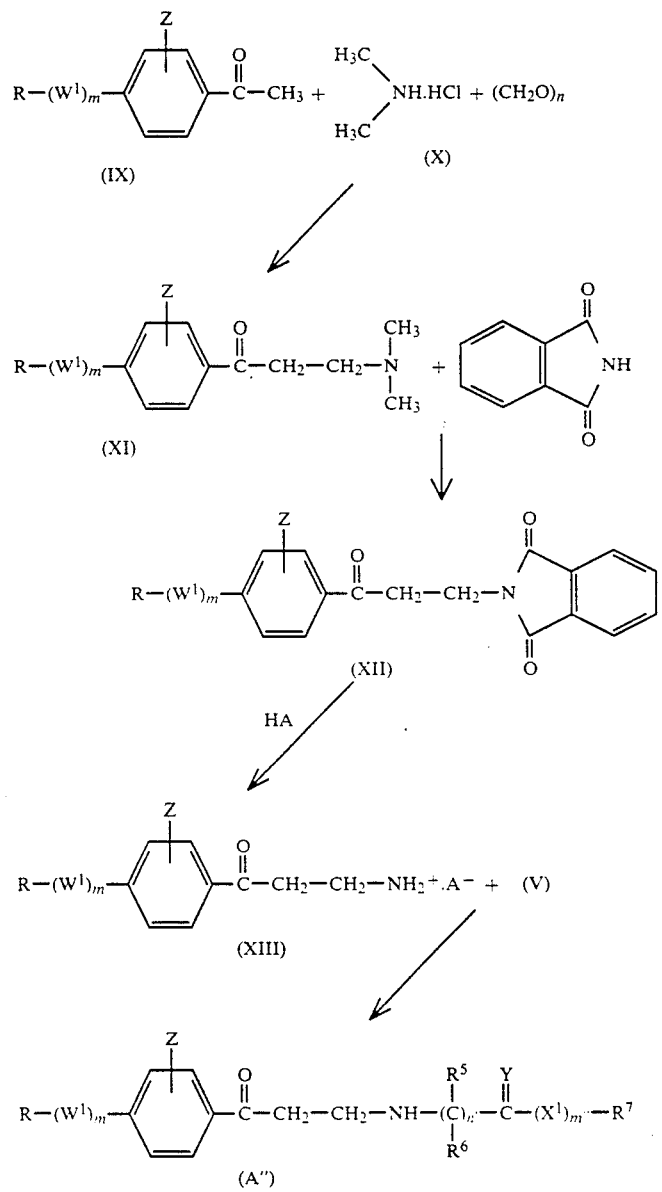

In the above synthesis, a 4-substituted acetophenone (IX) is treated with dimethylamine hydrochloride (X) and p-formaldehyde in a solvent such as 95% ethanol and under acidic conditions to give the β-aminopropiophenone (XI) which is reacted with phthalimide to give the β-phthalimidopropiophenone (XII). Compound XII is saponified under acidic conditions to give the β-aminopropiophenone acid salt, which is then reacted with a halide (V) following the general parameters and conditions described previously to give the final compound (A").

Compounds of formula A where $W^1$ is sulfinyl are prepared by reacting a compound of formula A where $W^1$ is sulfur with one equivalent of sodium periodate or m-chloroperbenzoic acid in a solvent such as methanol or methylene chloride. Compounds where $W^1$ is sulfonyl are prepared in the same manner, except that two equivalents of m-chloroperbenzoic acid are used. Alternatively, either hydrogen peroxide in warm acetic acid or excess hydrogen peroxide with selenium dioxide is used as the oxidant.

The compounds of the present invention of formula A can have one or more asymetric carbon atoms. The present invention includes each of the optical isomers and racemic mixtures thereof. In the examples hereinafter, unless otherwise specified, the compound prepared is a racemic mixture.

The compounds of the present invention of formula A are useful pest control agents, particularly for the control of insects, mites and ticks. The utility of these compounds as pest control agents is believed to be attributable to their juvenile hormone activity. They are preferably applied to the immature pest, namely during the embryo, larval or prepupal stage, in view of their effect on metamorphosis and otherwise abnormal development leading to death and inability to reproduce. These compounds can be effective control agents for insects of, for example, the orders Lepidoptera, Hemiptera, Homoptera, Coleoptera, Diptera, Orthoptera, and Siphonaptera, and other insects, as well as mites and ticks of the class Acari, including mites of the families Tetranychidae or Tarsonemidae and ticks of the families Argasidae and Ixodidae. The compounds can be applied to the pest or its locus in a pest controlling amount, usually of the order of 0.1 µg to 100 µg per insect, mite or tick.

In the use of the compounds of formula A for combatting pests, a compound of formula A, or mixtures thereof, can be combined with a carrier substance for application to the locus. The carrier can be liquid or solid and include adjuvants such as wetting agents, dispersing agents and other surface active agents. The compounds can be used in formulations such as wettable powders, solutions, dusts, granules, emulsifiable concentrates and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to 90.0 percent, by weight. Generally, a concentration of less than 25 percent of the active compound is employed.

The compounds of formula A can be combined with a cyclodextrin to make a cyclodextrin inclusion complex for application to the pest or its locus. The compounds of the present invention can be used in combination with other pesticides such as the synthetic pyrethroids, carbamates, phosphates and insect growth regulators, or with insect attractants.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to six halogen atoms.

The term "lower alkenyl" refers to an alkenyl group, straight or branched, having a chain length of two to eight carbon atoms and one or two ethylenic bonds. The term "lower haloalkenyl" refers to a lower alkenyl group substituted with one to six halogen atoms.

The term "lower alkynyl" refers to an alkynyl group, straight or branched, having a chain length of two to eight carbon atoms and one or two acetylenic bonds.

The term "lower haloalkynyl" refers to a lower alkynyl group substituted with one to six halogen atoms.

The term "lower alkoxyalkyl" refers to an alkyl group substituted at one of the carbon atoms by an alkoxy group, straight or branched, the total number of carbon atoms being not greater than ten.

The term "lower alkylthioalkyl" refers to a lower alkyl group substituted at one of the carbons atoms by an alkylthio group, straight or branched, the total number of carbon atoms being not greater than ten.

The term "cycloalkyl" refers to a cycloalkyl group of three to eight cyclic carbon atoms. The term "cycloalkylalkyl" refers to a cycloalkyl group wherein one hydrogen atom is replaced by a lower alkyl group, the total number of carbon atoms being from four to twelve. The term "halocycloalkyl" refers to a cycloalkyl group substituted with one to six halogen atoms.

The term "heterocycloalkyl" refers to a heterocycloalkyl group, saturated or unsaturated, of two to six carbon atoms and one to three atoms selected from nitrogen, oxygen or sulfur. The term "heterocycloalkylalkyl" refers to a heterocycloalkyl group wherein one hydrogen is replaced by a lower alkyl group, the total number of carbon atoms being from three to twelve.

The term "substituted phenyl" refers to a phenyl group substituted at one, two or three of the ring carbon atoms with a group selected from lower alkyl, lower haloalkyl, lower alkoxy, lower haloalkoxy, halogen, nitro, cyano and lower alkylthio.

The following examples are provided to illustrate the practice of the present invention. Temperature is given in degrees Centigrade. RT means room temperature.

EXAMPLE 1

A mixture of 4-(3-methyl-2-butenoxy)phenol (1.64 g, 9.2 mmol), ethyl 2-chloroethylcarbamate (1.81 g, 11.9 mmol), and potassium carbonate (2.54 g, 18.4 mmol) in 20 ml of dimethylformamide (DMF) is heated at 85° for 18 hours. The reaction mixture is cooled to room temperature (RT), poured into water and extracted with ether. The combined ether extracts are washed with water until neutral followed with brine and dried over calcium sulfate. The solvent was removed in vacuo and the residue was placed under high vacuum at 80° for ca. 2 hours to remove the excess ethyl 2-chloroethylcarbamate. Purification by preparative thin layer chromotography (prep. TLC) gave ethyl N-{2-[4-(3-methyl-2-butenoxy)phenoxy]ethyl }-carbamate (compound 1, Table A).

nmr CDCl$_3$ δ=1.23 (t, J=6Hz, 3H,—OCH$_2$CH$_3$), 1.77 (m, 6H, vinyl methyl), centered at 3.5 (m, 2H, methylene adjacent to NH), 4.03 (m, 4H, methylene adjacent to O), 4,39 (d, J=7Hz, 2H, vinyl methylene), centered at 5.25 (bm, 2H, NH and vinyl proton) and 6.8 (s, 4H, aromatic protons) ppm.

4-(3-Methyl-2-butenoxy)phenol is prepared by the addition of 3-methyl-2-butenyl bromide (3.38 g, 22.7 mmol) to hydroquinone (5.0 g, 45.4 mmol) and potassium carbonate (6.26 g, 45.4 mmol) in 50 ml of dimethylformamide (DMF) at RT. The mixture is heated to 80° and stirred for 20 hours. The reaction mixture is cooled and then added to ice water and hexane and the mixture is extracted with hexane (3X) to remove the bis ether by-product. The aqueous layer is then extracted with ether (3X) and the combined ether layers are washed with water and with brine and dried over calcium sulfate. The solvent is removed by rotoevaporation; the residue is diluted with chloroform and filtered to remove the insoluble hydroquinone, and the filtrate is collected and rotoevaporated to give the desired phenol.

Ethyl 2-chlroethylcarbamate is prepared by slowly adding (over 10 min.) 2-chloroethyl isocyanate (15.02 g, 142.0 mmol) to dry ethanol (16.5 ml, 13.0 g, 284.0 mmol) at 0°. The mixture is stirred at 0° for 1 hour, after which it is warmed to 50° and maintained at ~50° for approximately 15 min. After the reaction mixture is allowed to cool to RT, the ethanol is rotoevaporated off and the residue is put under high vacuum to give the carbamate.

EXAMPLE 2

Following the procedure of Example 1, each of the halides under column I is reacted with hydroquinone to give the corresponding phenol under column II, each of which phenol is then reacted with ethyl 2-chloroethyl-carbamate to yield the corresponding final product under Table A (compounds 2-11).

| | I |
|---|---|
| 2. | isopropyl iodide |
| 3. | 2-propynyl bromide |
| 4. | 4-pentynyl chloride |
| 5. | 3-chloro-2-propenyl chloride |
| 6. | 2-methyl-2-propenyl chloride |
| 7. | 3-trifluoromethyl-2-butenyl bromide |
| 8. | 4-methyl-3-pentenyl bromide |
| 9. | 3-chloro-2-butenyl chloride |
| 10. | 4-pentenyl bromide |
| 11. | ethoxymethyl chloride |
| | II |
| 2. | 4-isopropoxyphenol |
| 3. | 4-(2-propynoxy)phenol |
| 4. | 4-(4-pentynoxy)phenol |
| 5. | 4-(3-chloro-2-propenoxy)phenol |
| 6. | 4-(2-methyl-2-propenoxy)phenol |
| 7. | 4-(3-trifluoromethyl-2-butenoxy)phenol |
| 8. | 4-(4-methyl-3-pentenoxy)phenol |
| 9. | 4-(3-chloro-2-butenoxy)phenol |
| 10. | 4-(4-pentenoxy)phenol |
| 11. | 4-ethoxymethoxyphenol |

EXAMPLE 3

To ethyl N-{2-[4-(3-methyl-2-butenoxy)phenoxy]ethyl}-carbamate (0.60 g, 2.05 mmol) in methanol (7 ml) at ~40° is added mercuric acetate (0.67 g, 2.1 mmol) in methanol (8 ml) over 10 min. The mixture is stirred at 5° for 1 hour, then at 10°-15° for 30 min. Additional mercuric acetate (0.13 g, 0.41 mol) in methanol is added, and the mixture is allowed to stand at RT overnight. The mixture is then cooled to 3° and potassium hydroxide (0.57 g, 10.2 mmol) in methanol (4 ml) is added over 5 min., followed by addition of sodium borohydride (0.039 g, 1.02 mmol) in portions over 10 min. The resulting slurry is stirred at 3-5° for 45 min. Celite is added to the reaction mixture and the mercury is filtered off. Methanol is removed by rotoevaporation and ether and water are added to the residue. Following extraction with ether (3X), the ether extracts are combined and washed with water until neutral and with brine and dried over calcium sulfate. The crude product is filtered, rotoevaporated and purified by prep. TLC to yield ethyl N-{2-[4-(3-methoxy-3-methylbutoxy)-phenoxy]ethyl }carbamate (compound 12, Table A).

nmr (CDCl$_3$) δ 1.22 [t and s, 9H, OCH$_2$CH$_3$ and CH$_3$OC-(CH$_3$)$_2$CH$_2$CH$_2$O-], 1.92 [t, J=8Hz, 2H, CH$_3$OC(CH$_3$)$_2$CH$_2$O], 3.18 (s, 3H, CH$_3$O-), centered at 3.48 (m, 2H, methylene adjacent to —NH—), centered at 4.05 (m, 6H, methylene adjacent to —O—), 5.08 (bm, 1H, NH) and 6.8 (s, 4H, aromatic protons) ppm.

EXAMPLE 4

A mixture of hydroquinone (11.0 g, 100.0 mmol), ethyl 2-chloroethylcarbamate (7.6 g, 50.0 mmol), and potassium carbonate (13.8 g, 100.0 mmol) in 100 ml of dimethylformamide (DMF) is heated at 80° for 20 hours. After cooling to RT, the reaction mixture is poured into ice water and hexane, and the hexane layer is discarded to remove the bis ether by-product. The aqueous layer is then extracted with ether (3X) and the combined ether layers are washed with water, followed with brine, and dried over calcium sulfate. The solvent is removed and the residue is diluted with chloroform to precipitate out the excess hydroquinone. Following filtration, the filtrate is collected and rotoevaporated to give ethyl N-{2-(4-hydroxyphenoxy]-ethyl}carbamate, a solid.

To pre-washed sodium hydride (0.106 g, 4.4 mmol) in 5 ml of tetrahydrofuran (THF) and 5 ml of DMF at RT is added ethyl N-≡2-(4-hydroxyphenoxy]ethyl}carbamate (1.0 g, 4.4 mmol) in 5 ml of THF. The mixture is stirred at RT for 1.5 hours and is then cooled to −5°. 1-Methylpropyl bromide (0.72 g, 5.3 mmol) in 2 ml of THF is added to the mixture, followed by addition of 5 ml of DMF. The reaction mixture is allowed to warm slowly to RT, and is then heated at 60° for 18 hours. The reaction is cooled to RT and poured into water and the mixture is extracted with ether (3X). The combined ether layers are washed with water until neutral, followed with brine, and dried over calcium sulfate. The solvent is removed in vacuo and purification by prep. TLC yields ethyl N-{2-[4-(1-methylpropoxy)phenoxy]ethyl}carbamate (compound 13, Table A).

nmr (CDCl$_3$) δ=centered at 0.93 [m, 3H, CH$_3$CH$_2$CH(CH$_3$)-0], centered at 1.23 (t and d, 6H, CH$_3$CH$_2$CH(CH$_3$)—O— and OCH$_2$CH$_3$], centered at 1.56 [m, 2H, CH$_3$CH$_2$CH(CH$_3$)—O—], centered at 3.47 (m, 2H, methylene adjacent to NH—), centered at 4.03 (m, 5H, methylene and methine adjacent to —O—), centered at 5.07 (bm, 1, NH), and 6.77 (s, 4H, aromatic protons) ppm.

In the same manner, ethyl N-{2-(4-hydroxyphenoxy]ethyl}carbamate (1.25 g, 5.5 mmol) and sodium hydride, prewashed with pentane, (0.132 g, 5.5 mmol) are reacted together, followed by addition of 1-methylbutyl bromide. The mixture is heated at 50° for 20 hours, then worked up and purified by prep. TLC to give ethyl N-{2-[4-(1-methylbutoxy)phenoxy]ethyl}carbamate (compound 14, Table A).

nmr (CDCl$_3$) δ=centered at 0.9 [m, 3H, CH$_3$CH$_2$CH(CH$_3$)—O], centered at 1.23 [m, 6H, CH$_3$CH$_2$O—and CH$_3$CH$_2$CH$_2$CH(CH$_3$)—O] centered at 1.52 [m, 4H, CH$_3$CH$_2$CH$_2$CH—(CH$_3$)—], centered at 3.5 (m, 2H, methylene adjacent to NH), centered at 4.07 (m, 5H, methylene and methine adjacent to O—), centered at 5.12 (bm, 1, NH) and 6.8 (s, 4H, aromatic protons) ppm.

EXAMPLE 5

Following the procedures of Example 4, each of the halides under column III is reacted with ethyl N-{2-(4-hydroxyphenoxy]ethyl}-carbamate and sodium hydride to yield the corresponding final products (compounds 15-26, Table A).

III 15. 3-chloropropyl bromide
16. 3,3-dichloro-2-propenyl bromide
17. 1-ethylpropyl bromide
18. 1-methyl-2-butenyl bromide
19. 1,3-dimethylbutyl bromide
20. 2-methylbutyl chloride
21. 1-methylpentyl bromide
22. 3-chloro-1-propynyl chloride
23. 1,3-dimethyl-2-butenyl chloride
24. 3-methyl-2-pentenyl bromide
25. 2-chloro-2-propenyl bromide
26. cyclobutyl chloride

EXAMPLE 6

To ethyl N-{2[5-(3-methyl-2-butenoxy)phenoxy]ethyl}carbamate (0.46 g, 1.6 mmol) in 10 ml of methylene chloride at 5° is added m-chloroperbenzoic acid (0.29 g, 1.7 mmol) in portions over 15 min. The mixture is stirred at 5° for 1 hour, then allowed to warn to RT and stirred for 1.5 hours longer. Ether is added to the reaction mixture and it is poured into water and washed with 10% sodium sulfite, with saturated sodium bicarbonate, with water until neutral and with brine. The organic layer is dried over calcium sulfate, filtered and rotoevaporated and the residue is purified by Florisil column chromatography to give ethyl N-{2-[4-(3-methyl-2,3-epoxybutoxy)phenoxy]ethyl }carbamate (compound 27, Table A).

EXAMPLE 7

To 2,2,2-trifluoroethanol (5.0 g, 50.0 mmol) and triethylamine (10.5 ml, 7.6 g, 75.0 mmol) in 25 ml of ethylene chloride at −10° is added methanesulfonyl chloride (4.25 ml, 6.3 g, 55.0 mmol) over 20 min. maintaining the temperature at 0° to −10°. After addition is complete, the mixture is stirred at 0°-5° for 30 min. It is then poured into ice water and additional methylene chloride is added. The layers are separated, and the methylene chloride layer is washed with cold 10% HCl, with cold saturated sodium bicarbonate, with cold water until neutral, and with cold brine. The organic layer is dried over calcium sulfate with swirling and is filtered and the solvent is removed to give 2,2,2-trifluoroethyl methansulfonate.

To prewashed sodium hydride (0.61 g, 25.5 mmol) in 10 ml of hexamethylphosphorotriamide (HMPT) is added 4-nitrophenol (3.55 g, 25.5 mmol) in 10 ml of HMPT at 25°-30°. Five ml more of HMPT is added and the mixture is warmed gently to 45°-50° for 30 min. 2,2,2-Trifluoroethyl methansulfonate (5.0 g, 28.0 mmol) and HMPT (1 ml) are then added and the mixture is heated to 146°-151° for 20 hours. The reaction mixture is cooled to RT and is then poured into ice water and extracted with ether (3X). The combined ether layers are washed with water and brine, dried, filtered and rotoevaporated to give 4-(2,2,2-trifluoroethoxy)nitrobenzene.

To the above substituted nitrobenzene (2.5 g, 11.3 mmol) and ammonium chloride (6.04 g, 113.0 mmol) in 57 ml of ethanol and 35 ml of water at 65° and under $N_2$ is added iron dust (3.16 g, 56.6 mmol) in portions over 20 min. The slurry is stirred at 70° for 1.5 hours. The mixture is slowly cooled to RT and filtered through celite with additional ethanol washes. The ethanol is removed by rotoevaporation; ether and water are added and the water layer is extracted with ether (3X). The combined organic layers are washed with water and brine, dried, filtered and rotoevaporated to give 4-(2,2,2,-trifluoroethoxy)aniline.

The above substituted aniline (1.64 g, 8.6 mmol) is added to 6N sulfuric acid (20 ml) at 3°, followed by slow addition of sodium nitrate (0.59 g, 8.6 mmol) in 1.5 ml of water. The mixture is stirred at 3°-5° for 1 hour and is then heated slowly to 100°-110° and held at 110° for 2 hours. After cooling to RT, the reaction is poured into water and ether, and the ether extracts are washed, dried and rotoevaporated to give 4-(2,2-trifluoroethoxy)phenol.

Following the procedure of Example 1, 4-(2,2,2-trifluoroethoxy)phenol (0.42 g, 2.2 mmol) and ethyl N-(2-chloroethyl)carbamate (0.40 g, 2.6 mmol) are reacted together to give ethyl N-{2-[4-(2,2,2-trifluoroethoxy)phenoxy]ethyl}carbamate (compound 28, Table A).

Following the above procedures, 1-trifluoromethylethyl methanesulfonate is reacted with 4-nitrophenol to give 4-(1-trifluoromethylethoxy)phenol, which is then reacted with ethyl N-(2-chloroethyl)carbamate to give ethyl N-{2-[4-(1-trifluoromethylethoxy)phenoxy]ethyl}carbamate (compound 29, Table A).

EXAMPLE 8

Chloroacetone (0.89 ml, 1.04 g, 11.2 mmol) is added to a mixture of 4-(3-methyl-2-butenoxy)phenol (2.0 g, 11.2 mmol), potassium carbonate (25 g) and potassium iodide (2.6 g) in 125 mol of anhydrous acetone. The mixture is heated under reflux for 4.5 hours and then is allowed to cool to RT to give 4-(3-methyl-2-butenoxy)-phenoxyacetone.

Ammonium acetate (3.29 g, 42.7 mmol), sodium cyanoborohydride (0.20 g, 3.0 mmol) and 3A molecular sieves are added to the above phenoxyacetone (1.0 g, 4.3 mmol) in 20 ml of anhydrous methanol under $N_2$ and at RT. The reaction is stirred at RT for 4 days. The methanol is removed by rotoevaporation, and ether and water are added to the residue, followed by 10% NaOH. The mixture is extracted with ether (3X), and the combined organic layers are washed with water until neutral, dried and filtered and the solvent evaporated off to give 2-[4-(3-methyl-2-butenoxy)phenoxy]-1-methylethylamine.

To the above amine (0.86 g, 3.7 mmol) and pyridine (0.64 g, 8.0 mmol ) in 8 ml of ether at 5° is added dropwise over 10 min. ethyl chloroformate (0.43 g, 4.0 mmol) in 2 ml of ether. The mixture is stirred at 5° for 1 hour and is then allowed to warm to RT. Excess ethyl chloroformate is quenched with water and the reaction mixture is poured into water and ether and the aqueous phase is extracted with ether (3X). The combined organic layers are washed with 2N ammonium sulfate, with 10% sodium carbonate, then with water until neutral and with brine. The organic layer is dried, filtered, the solvent removed and the product purified by prep. TLC to give ethyl N-{2-[4-(3-methyl-2-butenoxy)phenoxy]-1-methylethyl}carbamate m/s ($M^+$) 307.

EXAMPLE 9

4-(1-Methylpropoxy)phenol (6.92 g, 41.6 mmol), ethylene carbonate (7.34 g, 83.2 mmol) and DMF (456 ml) are mixed under $N_2$. With stirring, the mixture is degassed (3X) by alternate application of vacuum and $N_2$. Potassium carbonate (11.51 g, 83. 2 mmol) is then added, under $N_2$, and the mixture is heated at 90° for 27 hours. The reaction mixture is then poured into ice water and 10 ml of 40% potassium carbonate solution is added to increase the pH to 13. The aqueous phase is extracted with ether (3X) and the organic layers are washed with 40% KOH, the water until neutral and with brine, dried, filtered and the solvent evaporated to give 2-[4-(1-methylpropoxy)phenoxy]ethanol.

Dibutyltin diacetate (0.004 ml) is added to a solution of the above alcohol (0.42 g, 2.0 mmol) in 1.5 ml of DMF and the mixture is chilled in an ice bath. Ethyl isocyanate (0.18 ml, 2.2 mmol) is then added and the mixture is allowed to warn slowly to RT. The mixture is then poured into ether and water containing 10% potassium dihydrogen phosphate. The aqueous phase is extracted with ether, and the combined organic phases are washed with water and with brine, dried, filtered and the solvent is removed in vacuo to give O-2-[4-(1-methylpropoxy)phenoxy]-ethyl N-ethylcarbamate (compound 30, Table A).

EXAMPLE 10

Following the procedures of Example 9, each of the phenols under column IV is reacted with ethylene carbonate to give the corresponding substituted-phenoxyethanol, which is then reacted with ethyl isocyanate to give the corresponding carbamate under Table A (compounds 31–35).

IV 31. 4-(3methyl-2butenoxy)phenol
32. 4-(1methylbutoxy)phenol
33. 4-(2methylbutoxy)phenol
34. 4-(2-chloro-2-propenoxy)phenol
35. 4-(1-methylpentoxy)phenol

EXAMPLE 11

To sodium hydride (0.15 g, 6.0 mmol), prewashed with pentane, in 5 ml of DMF and cooled in an ice bath, is added 2-[4-(1-methylpropoxy)phenoxy]ethanol (1.26 g, 6.0 mmol) in 5 ml of DMF. The mixture is stirred for 20 min. at ca. 5°, after which is it heated to 50° for 20 min. The mixture is again cooled to ca. 5° and ethyl isothiocyanate (0.58 ml, 6.0 mmol) and 5 ml DMF are added. After 1 hour at 5°, the mixture is allowed to warn to RT, and any residual sodium hydride is destroyed by addition of 2 drops of methanol. The reaction mixture is poured into water and acidified with 3N sulfuric acid. The aqueous phase is extracted with ether (3X), and the combined organic phases are washed with water, with 10% sodium bicarbonate, with water and with brine, dried and filtered and the filtrate is concentrated in vacuo to give, after purification with prep. TLC, O-2-[4-(1-methylpropoxy)phenoxy]-ethyl N-ethylthiocarbamate (compound 36, Table A).

In the same manner, 2-[4-(3-methyl-2-butenoxy)phenoxy]-ethanol is reacted with sodium hydride and ethyl isothiocyanate to yield O-2-[4-(3-methyl-2butenoxy)phenoxy]ethyl N-ethylthiocarbamate (compound 37, Table A).

EXAMPLE 12

Potassium t-butoxide (30.6 g, 275.0 mmol) is added to a solution of 4-methoxybenzenethiol (30.0 ml, 250.0 mmol) in 250 ml of DMF. The mixture is heated at 80° until homogeneous, after which 2-bromobutane (30.0 ml, 275.0 mmol) in 30 ml of DMF is added dropwise over approx. 30 min. The mixture is stirred at 60° overnight after which it is cooled and is then poured into water and the aqueous phase is extracted with ether (3X). The combined ether extracts are washed with water, with 5% sodium hydroxide, with water and with brine, dried and the solvent removed to give 4-(1-methylpropylthio)anisole.

To sodium hydride (6.6 g, 275.0 mmol; prewashed with pentane) in 100 ml of DMF, under $N_2$ and at 5°, is slowly added ethyl mercaptan (41.0 ml, 550.0 mmol) in 50 ml of DMF. This mixture is stirred for 1.5 hours, after which is added 4-(1-methylpropylthio)anisole (46.0 g, 250.0 mmol) and DMF. The mixture is heated to 150° with stirring overnight. After cooling to 20°, 10% aqueous sulfuric acid is added and the mixture is extracted with ether. The combined organic layers are washed with water and extracted with 5% NaOH. The aqueous portion is reacidified with conc. sulfuric acid and extracted with ether. The combined ether extracts are washed with water and with brine, dried and the solvent removed to give 4-(1-methylpropylthio)phenol.

A mixture of ethylene carbonate (41.08 g, 460.0 mmol) and potassium carbonate (63.57 g, 460.0 mmol) in 100 ml of DMF is heated to 110° and 4-(1-methylpropylthio)phenol (40.19 g, 230.0 mmol) in 100 ml DMF is slowly added dropwise with stirring. The mixture is stirred at 100° for 8 hours. Water is added to the cooled reaction mixture and the aqueous phase is extracted with ether. The combined organic layers are washed with 5% NaOH, with water and with brine, dried and the solvent removed to give 2-[4-(1-methylpropylthio)phenoxy]ethanol.

A mixture of the above alcohol (2.16 g, 10.0 mmol) and potassium carbonate (1.66 g, 12.0 mmol) in 10 ml of DMF is cooled to 5° and ethyl isothiocyanate (1.10 ml, 12.0 mmol) in 10 ml of DMF is added dropwise. After addition is complete, the mixture is allowed to warm to RT and is stirred at RT overnight. Water is added and the aqueous phase is extracted with ether. The combined organic layers are washed with water and brine, dried, the solvent removed and the residue is purified by column chromatography to give O-2-[4-(1-methylpropylthio)phenoxy]ethyl N-ethylthiocarbamate (compound 38, Table A).

nmr (CDCl$_3$) δ 7.37 (d, 2, J=8.8 Hz, phenyl), 7.24–7.00 (bs, 0.6, NH), 6.83 (d, 2, J=9, phenyl), 6.54–6.40 (bs, 0.4, NH), 4.77 (m, 2, OHC$_2$CH$_2$O), 4.19 (m, 2, OCH$_2$CH$_2$O), 3.68–3.21 (m, 2, NHCH$_2$CH$_3$), 2.97 (sextuplet, 1, J=6.4, CHS), 1.55 (m, 2, CH$_2$CHS), 1.20 (d, 3, J=6.6, CH$_3$CHS), 1.19 (t, 3, J=6.4, NHCH$_2$CH$_3$) and 0.98 ppm (t, 3, J=6.8, CH$_3$CH$_2$CHS).

Following the above procedure, 2-[4-(1-methylpropylthio)phenoxy]ethanol (2.16 g, 10.0 mmol) is reacted with ethyl isocyanate (1.5 ml, 18.0 mmol) to give O-2-[4-(1-methylpropylthio)phenoxy]ethyl N-ethylcarbamate (compound 39, Table A).

nmr (CDCl$_3$) δ 7.37 (d, 2, J=8.4 Hz, phenyl), 6.84 (d, 2, J=8.4 Hz, phenyl), 4.80 (bs, 1, NH), 4.25 (m, 2, OCH$_2$CH$_2$O), 4.08 (m, 2, OCH$_2$CH$_2$O), 3.60–2.80 (m, 3, CH$_2$CHS, NHCH$_2$CH$_3$), 1.28 (m, 2, CH$_2$CHS), 1.24–1.13 (m, 6, CH$_3$CHS, NHCH$_2$CH$_3$) and 0.98 ppm (t, 3, J=6.6 Hz, CH$_3$CH$_2$CHS).

Alternatively, the procedure in Example 9 can be used to prepare the above compound 39.

EXAMPLE 13

To a mixture of 2-[4-(1-methylpropylthio)phenoxy]ethanol (4.26 g, 20.0 mmol) and triethylamine (4.2 ml, 30.0 mmol) in 100 ml methylene chloride at 0° is added dropwise methanesulfonyl chloride (1.7 ml, 22.0 mmol). The mixture is stirred at 0° for 20 min, after which it is poured into ice water. The methylene chloride layer is washed with ice water, with cold 10% sulfuric acid, with cold 5% sodium bicarbonate and with cold brine, dried and the solvent removed to give 2-[4-(1-methylpropylthio)phenoxy]ethyl methanesulfonate.

The above sulfonate (5.76 G, 20.0 mmol) is added dropwise to a mixture of phthalimide (3.70 g, 25.0 mmol) and potassium carbonate (4.10 g, 30.0 mmol) in 50 ml of DMF and under $N_2$. The resulting mixture is heated to 60° for 9 hours, with stirring, and is then stirred at 40° overnight. After cooling, water is added to the reaction mixture and the aqueous phase is extracted with ether (3X). The combined organic layers are washed with water and with brine, dried and rotoevaporated to give N-{2-[4-(1-methylpropylthio)-phenoxy]ethyl}phthalimide.

To a solution of the above phthalimide (6.84 g, 19.7 mmol) in 100 mol of ethanol, heated to 60°, is added hydrazine hydrate (2.0 ml, 41.0 mmol) with stirring. Additional ethanol (100 ml) is added and the mixture is stirred overnight at 60°. After cooling, 5% sodium hydroxide is added and the basic mixture is extracted with ether. The combined organic layers are washed with water and brine, dried and rotoevaporated to give 2-[4-(1-methylpropylthio)phenoxy]ethylamine.

To a solution of the above amine (2.41 g, 10.0 mmol) in 10 ml DMF, cooled to 0° and under $N_2$, is added potassium carbonate (1.66 g, 12.0 mmol) followed by dropwise addition of ethyl chloroformate (1.2 ml, 12.0 mmol) in 5 ml of DMF. After 1.5 hours, water is added and the aqueous phase is extracted with ether. The combined organic layers are washed with water and brine, dried, rotoevaporated and the residue is purified by column chromatography to give ethyl N-{2-[4-(1-methylpropylthio)phenoxy]ethyl}carbamate (compound 40, Table A).

nmr (CDCl$_3$) δ 7.37 (d, 2, J=8.8 Hz, phenyl), 6.81 (d, 2, J=8.8, phenyl), 5.28-5.00 (s, 1, NH), 4.05 (q, 2, J=6.6, OCH$_2$CH$_3$), 4.01 (m, 2, OCH$_2$CH$_2$NH), 3.60 (m, 2, OCH$_2$CH$_2$NH), 2.99 (m, 1, J=6.4, CH$_2$CHS), 1.46 (m, 2, CH$_3$CHS) and 0.98 ppm (t, 3, J=6.8, CH$_3$CH$_2$CH).

EXAMPLE 14

Following a modification of the procedure of Example 12 (using RT instead of 60° for the first step), 2-[4-(3-methyl-2-butenylthio)phenoxy]ethanol is prepared and is reacted with each of ethyl isothiocyanate and ethyl isocyanate to yield, respectively, O-2-[4-(3-methyl-2-butenylthio)phenoxy]ethyl N-ethylthiocarbamate (compound 41, Table A), and O-2-[4-(3-methyl-2-butenylthio)phenoxy]ethyl N-ethylcarbamate (compound 42, Table A).

EXAMPLE 15

Following the procedure of Example 13, 2-[4-(3-methyl-2-butenylthio)phenoxy]ethylamine is prepared and is reacted with ethyl chloroformate to give ethyl N-{2-[4-(3-methyl-2-butenylthio)phenoxy]ethyl}carbamate (compound 43, Table A).

EXAMPLE 16

To 4-(1-methylpropylthio)benzenethiol (8.79 g, 44.3 mmol) in 25 ml of DMS is added, under $N_2$, potassium carbonate (7.05 g, 51.0 mmol) followed by dropwise addition of N-(bromoethyl)-phthalimide (12.94 g, 51.0 mmol) in 30 ml of DMF. The mixture is stirred at RT overnight. Water is then added and the aqueous phase is extracted with ether. The combined organic layers are washed with 5% sodium hydroxide, with water and with brine, dried and the solvent removed to give N-{2-[4-(1-methylpropylthio)-phenylthio]ethyl}phthalimide.

Following the procedures of Example 13, the above phthalimide (2.12 g, 5.7 mmol is reacted with hydrazine hydrate (0.28 ml, 5.7 mmol) to give 2-[4-(1-methylpropylthio)phenylthio ethylamine.

Following the procedures of Example 13, the above amine is reacted with each of ethyl chloroformate and ethyl chlorothioformate to give, respectively, ethyl N-{2-[4-(1-methylpropylthio)phenylthio]ethyl}carbamate (compound 44, Table A), and S-ethyl N-{2-[4-(1-methylpropylthio)phenylthio]ethyl}thiocarbamate (compound 45, Table A).

4-(1-Methylpropylthio)benzenethiol is prepared by the following method. 1-Bromo-4-(1-methylpropylthio)benzene (17.63 g, 72.0 mmol) in 100 ml of ether is added dropwise to magnesium (2.12 g, 86.0 mmol) in 20 ml of ether. Early in the addition, a catalytic amount of 1,2-dribromobutane is added. The mixture is then heated under reflux overnight, after which it is cooled to RT and sulfur (1.96 g, 61.0 mmol) is added portionwise. The mixture is then heated to 30°-35° for ca. 2 hours and is then cooled to −5°. 2.5 N aqueous HCl (150 ml) is added dropwise while maintaining the temperature at ca. 0°. The layers are separated and the organic layer is washed with 5% sodium hydroxide. This basic aqueous layer is reacidified with conc. sulfuric acid and is extracted with ether (3X). The combined ether extracts are washed with water and with brine, dried and rotoevaporated to give 4-(1-methylpropylthio)benzenethiol.

1-Bromo-4-(1-methylpropylthio)benzene is prepared by the following procedure. To a solution of 4-bromobenzenethiol (4.73 g, 25.0 mmol) in 25 ml of DMF at 70° under $N_2$ is added potassium carbonate (4.15 g, 30.0 mmol). The mixture is allowed to stir for 15 min., after which 3-bromobutane (4.8 ml, 44.0 mmol) is added dropwise. The mixture is stirred at 70° for ca. 5 hours. Water is added to the cooled solution and the aqueous phase is extracted with ether (3X). The combined organic layers are washed with water and with brine and dried and the solvent is removed in vacuo to give, following purification by distillation under vacuum, 1-bromo-4-[1-methylpropylthio)benzene.

Following the above procedures, 2-[4-(3-methyl-2-butenylthio)phenylthio]ethylamine is prepared from 4-(3-methyl-2-butenylthio)benzenethiol and is reacted with each of ethyl chloroformate and ethyl chlorothioformate to give, respectively, ethyl N-{2-[4-(3-methyl-2-butenylthio)phenylthio]ethyl}carbamate (compound 46, Table A), and S-ethyl N-{2-[4-(3-methyl-2-butenylthio)phenylthio]ethyl}thiocarbamate (compound 47, Table A).

In a similar manner, 2-[4-(1-methylpropoxy)phenoxy]-ethylamine, 2-[4-(3-methyl-2-butenoxy)phenoxy]ethylamine and 2-[4-(1-methylpropylthio)phenoxy]ethylamine are prepared from, respectively, 4-(1-methylpropoxy)phenol, 4-(3-methyl-2-butenoxy)phenol and 4-(1-methylpropylthio)phenol. Each of the above amines is reacted with S-ethyl chlorothioformate to yield, respectively, S-ethyl N-{2-[4-(1-methylpropoxy)phenoxy]ethyl}thiocarbamate (compound 48, Table A), S-ethyl N-{2-[4-(3-methyl-2-butenoxy)phenoxy]ethyl}thiocarbamate (compound 49, Table A), and S-ethyl N-{2-[4-(1-methylpropylthio)-phenoxy]ethyl}thiocarbamate (compound 83, Table A).

EXAMPLE 17

Following a modification of the procedure of Example 12 (without potassium carbonate), each of 2-[4-(1-methylpropylthio)phenylthio]ethylamine, 2-[4-(3-methyl-2-butenylthio)phenylthio]ethylamine and 2-[4-(3-methyl-2-butenoxy)phenoxy]ethylamine is reacted with ethyl isothiocyanate to yield, respectively, N-{2-[4-(1-methylpropylthio)phenylthio]ethyl}-N'-ethylthiourea (compound 40), N-{2-[4-(1-methylpropoxy)phenoxy]ethyl}-N'-ethylthiourea (compound 51).

N-{2-[4-(3-methyl-2-butenylthio)phenylthio]ethyl}-N'-ethylthiourea (compound 52), and N-{2-[4-(3-methyl-2-butenoxy)phenoxy]ethyl}-N'-ethylthiourea (compound 53, Table A).

In the same manner, each of the above four amines is reacted with ethyl isocyanate to give the corresponding urea (compounds 54, 55, 56 and 57, respectively, under Table A).

EXAMPLE 18

To a mixture of 4-(1-methylpropylthio)benzenethiol (53.7 g, 271.0 mmol) and potassium carbonate (49.4 g, 358.0 mmol) in DMF under $N_2$ and with stirring is added dropwise 2-bromoethyl acetate (34.0 ml, 298.0 mmol). The mixture is stirred at RT overnight, after which water is added and the mixture is extracted with ether. The combined organic layers are washed with water and brine, dried, the solvent removed and the residue purified by distillation to give 2[4-(1-methylpropylthio)phenylthio]ethyl acetate. To the acetate (60.9 g, 214.0 mmol) in 200 ml of ethanol is added 50% sodium hydroxide (20 ml). The reaction mixture is stirred at RT for 7 hours and is then neutralized by addition of 10% sulfuric acid and extracted with ether. The organic layer is washed with water and brine, dried and the solvent removed to give 2-[4-(1-methylpropylthio)phenylthio]ethanol.

Following the above procedure, 2-[4-(3-methyl-2butenylthio)phenylthio]ethanol is prepared from 4-(3-methyl-2butenylthio)benzenethiol and 2-bromoethyl acetate.

Following a modification of the procedure of Example 12, each of the alcohols under column V is reacted with ethyl chloroformate, in the presence of pyridine, to give the corresponding carbonate (compounds 58–63, Table A).

V 58. 2-[4(1-methylpropylthio)phenylthio]ethanol
59. 2-[4(1-methylpropylthio)phenoxy]ethanol
60. 2-[4(1-methylpropoxy)phenoxy]ethanol
61. 2-[4(3-methyl-2-butenylthio)phenylthio]ethanol
62. 2-[4(3-methyl-2-butenylthio)phenoxy]ethanol
63. 2-[4(3-methyl-2-butenoxy)phenoxy]ethanol In the same manner, S-ethyl chlorothioformate is reacted with each of 2-[4(1-methylpropylthio)phenylthio]ethanol, 2-[4(1-methylpropoxy)phenoxy]ethanol, 2-[4(3-methyl-2-butenylthio)phenylthio]ethanol and 2-[4(1-methylpropylthio)phenoxy]ethanol to give, respectively, compounds 64, 65, 66, 67 and 84 under Table A.

EXAMPLE 19

Carbon disulfide (15 ml) is added dropwise to 2-[4-(1-methylpropylthio)phenylthio]ethylamine (2.42 g, 10.0 mmol) at 0° and under $N_2$. After addition is complete, potassium hydroxide (0.67 g, 12.0 mmol) is added. The mixture is heated under reflux for 4 hours, with stirring, after which it is cooled, and diluted with ether and the solvent is removed to give the potassium salt of N-[4-(1-methylpropylthio)phenylthioethyl]dithiocarbamic acid. To this salt (10.0 mmol) dissolved in 30 ml of DMF is added iodoethane (1ml, 12.5 mmol), under $N_2$ and with stirring. The mixture is stirred at RT overnight and is then worked up by addition of water and extraction with ether. The ether layer is washed with 10% sulfuric acid, with water and with brine, dried, the solvent removed and the product is purified by column chromatography to give S-ethyl N-{2-[4-(1-methylpropylthio)phenylthio]ethyl}dithiocarbamate (compound 68, Table A).

In the same way, each of 2-[4-(1-methylpropoxy)phenoxy]-ethylamine, 2-[4-(3-methyl-2-butenylthio)phenylthio]ethylamine, 2-[4-(3-methyl-2-butenoxy)phenoxy]ethylamine and 2-[4-(1-methylpropylthio)phenoxy]ethylamine is reacted with carbon disulfide and potassium hydroxide, followed by iodoethane to give the corresponding dithiocarbamate (compounds 69, 70, 71 and 86, respectively, under Table A).

Likewise, following the same procedure, carbon disulfide and potassium hydroxide, followed by iodoethane, are reacted with each of 2-[4-(1-methylpropylthio)phenylthio]ethanol, 2-[4-(1-methylpropoxy)phenoxy]ethanol, 2-[4-(3-methyl-2-butenylthio)phenylthio]ethanol, 2-[4-(3-methyl-2-butenoxy)phenoxy]ethanol and 2-[4-(1-methylpropylthio)phenoxy]ethanol to yield the corresponding compounds 72, 73, 74, 75 and 85, respectively, under Table A.

EXAMPLE 20

To a solution of 2-[4-(1-methylpropoxy)phenylthio]-ethylamine (2.21 g, 8.65 mmol) in 25 ml of ether, at 0° and under $N_2$, is added ethyl chloroformate (0.52 g, 4.76 mmol) by syringe, followed by addition of 10% aqueous sodium hydroxide (3.5 ml) and additional ethyl chloroformate (0.51 g, 4.76 mmol). After 15 min., the reaction is worked up by addition of water and extraction with ether. The combined organic phases are washed with 1N sulfuric acid, with water and with brine, dried and filtered, the filtrate is concentrated in vacuo and the product is purified by prep. TLC to give ethyl N-{2-[4-(1-methylpropoxy)-phenylthio]ethyl}carbamate (compound 76, Table A).

In the same manner, 2-[4-(3-methyl-2-butenoxy)-phenylthio]ethylamine is reacted with ethyl chloroformate to yield ethyl N-{2-[4-(3-methyl-2-butenoxy)-phenylthio]ethyl}carbamate (compound 77, Table A).

Each of 2-[4-(1-methylpropoxy)phenylthio]ethylamine and 2-[4-(3-methyl-2-butenoxy)phenylthio]ethylamine is prepared by the reaction of, respectively, 4-(1-methylpropoxy)-benzenethiol and 4-(3-methyl-2-butenoxy)benzenethiol with N-(2-bromoethyl)phthalimide, followed by treatment with hydrazine hydrate, following the procedure of Example 16.

EXAMPLE 21

The compounds ethyl N-{2-[4-(3-methoxy-3-methylbutoxy)-phenoxy]ethyl}carbamate (compound 12), ethyl N-{2-[4-(1-methylpropoxy)phenoxy]ethyl}carbamate (compound 13), O-2-[4-(1-methylpropoxy) phenoxy]ethyl N-ethylcarbamate (compound 30) and O-2-[4-(1-methylpropoxy)phenoxy]ethyl N-ethylthiocarbamate (compound 36) were tested for contact activity on houseflies by the following method.

Third instar, post-feeding wandering *Musca domestica* L. Larvae are individually treated with 1µl of the test compound in acetone at different dose rates. Additional larvae are treated identically with 1µl of acetone as the control. Larvae are held in covered containers for 7 days at 31° and 16 hour photoperiod. The assay effect is expressed as $ED_{50}$, which is the dose, in µg per larva, required to cause an effect in 50% of the test insects. Effects observed include direct toxicity (larval death); delayed toxicity (pupal death); and juvenile hormone activity, such as failure of adults to emerge completely, chitin inhibition, distortion of cuticle and pupation abnormalities. Each of the above tested compounds had an $ED_{50}$ of <0.030 µg/larva.

EXAMPLE 22

The compounds ethyl N-{2-[4-(3-methyl-2-butenoxy)phenoxy]-ethyl}carbamate (compound 1), O-2-[4-(1-methylpropoxy)phenoxy]ethyl N-ethylcarbamate (compound 30), O-2-[4-(1-methylpropylthio)phenoxy]ethyl N-ethylthiocarbamate (compound 38) and O-2[4-(1-methylpropylthio)phenoxy]ethyl N-ethylcarbamate (compound 39) were tested for activity on the yellow fever mosquito as follows.

Late fourth instar *Aedes aegypti* larvae (generally 5 days post-hatching) are placed in plastic containers with 50 ml tap water into which has been mixed 50 µl of acetone dilution of the test compound at the concentration to be tested. A few drops of a liver powder suspension are added as a food source. The containers are covered and held at 28°, 16 hour photoperiod until all larvae or pupae are either dead or have emerged as adults. The assay effect is expressed as $EC_{50}$, which is the concentration, in ppm, required to cause an effect in 50% of the test insects. Effects observed include direct toxicity (larval death) and juvenile hormone activity such as pupal mortality and failure of adults to emerge completely. Each of the above tested compounds had an $EC_{50}$ of <0.010 ppm.

EXAMPLE 23

Activity of the compounds ethyl N-{2-[4-(1-methylpropoxy)-phenoxy]ethyl}carbamate (compound 13), O-2-[4-(1-methylpropylthio)-phenoxy]ethyl N-ethylthiocarbamate (compound 3) and O-2-[4-(1-methylproplythio)phenoxy]ethyl N-ethylcarbamate (compound 39) when ingested by the German cockroach was tested as follows.

Treated food is prepared by mixing the test compound into GAINESBURGER® dog food at the dosage rates to be tested. One hundred 3instar *Blatella germanica* nymphs are placed in a cage whose sides are treated with FLUON® to prevent escape of any roaches. Water and harborage are provided and a constant supply of the treated dog food is maintained. A control with untreated dog food is also run. The cages are kept at 28°, 16 hr. photoperiod and 50% relative humidity. The roaches are observed for the development of normal and abnormal adults. Normal adults are those which have fully developed wings of the normal flat shape. Also observed is the percent control of reproduction. At 10 ppm, each of the about compounds gave 100% control of reproduction.

EXAMPLE 24

Activity of the compounds ethyl N-{2-[4-(3-methyl-2-butenoxy)-phenoxy]ethyl}carbamate (compound I) and ethyl N-{2-[4-(1-methyl-propoxy)phenoxy]ethyl} carbamate (compound 13) on the cat flea was tested as follows.

The inside bottoms of glass petri dishes 20 mm × 100 mm dishes) are treated with 1 ml of an acetone dilution of the test compound at the concentration to be tested. Approximately one hour after treatment, ⅛ teaspoon of flea rearing medium, consisting of 50% sterilized sand and 50% finely ground flea food, is placed into each dish. The flea food consists of 4:1 Purina® cat chow to dried beef blood. Five one-week-old final instar larvae of cat fleas, *Ctenocephalides felis*, are placed into each dish, covered and held at 27° and 80% relative humidity for 35 days. At 35 days post treatment, counts of flea adults, pupae and larvae are taken. The assay effect is expressed as the percent inhibition of adult emergence. At $3.5 \times 10^{-5}$ mg/ml, or 0.0005 mg/ft² of glass surface, each of the above compounds gave 100% control of adult emergence.

EXAMPLE 25

To isopropenyl methyl ether (10.0 g, 139 mmol) and 18-crown-6 ether (0.85 g, 3.2 mmol) in 55% aqueous KOH (28.9 g of KOH, 535 mmol) at −15° is added dichlorofluoromethane (37.2 g, 361 mmol) over 20 mins. After the addition, the reaction is warmed to 0° and stirred for 2 hours, and then water is slowly added until the solid formed during the reaction just dissolves. The reaction is warmed to RT and excess dichloroformethane is removed. The organic layer is separated and distilled to give a syn and anti mixture of 1-chloro-1-fluoro-2-methoxy-2-methyl cyclopropane [46°–48° (65 mm)].

A mixture of 1-chloro-1-fluoro-2-methoxy-2-methyl-cyclopropane (12.5 g, 90.2 mmol) and a trace of hydroquinone (0.028 g) in 25 ml of 0.015 M sodium dodecyl sulfate solution is heated to a gentle reflux. The reaction product is then distilled off continuously along with MeOH, as they are formed, in a slow stream of nitrogen over 6 hrs. to give 2-fluoro-1-buten-3-one.

The mixture of 2-fluoro-1buten-3-one (approx. 1 g, 11.4 mmol), and methanol is added to sodium borohydride (0.218 g, 5.7 mmol) in 10% aqueous MeOH (10 ml) at 55°. The reaction is heated for 20 mins. and then cooled and worked up by pouring into water end extracting with ether. The combined ether layers are washed with water and brine, dried over calcium sulfate, and filtered. The ether is distilled off to give 2-fluoro-1-buten-3-ol.

To 2-fluoro-1-buten-3-ol (0.5 g, 5.5 mmol) in 10 ml of ether at −15°is slowly added phosphorus tribromide (0.496 g, 1.8 mmol). The reaction is stirred at 31 15° for 1 hr. and is then slowly warmed to RT over 1.5 hrs. The product is isolated by pouring the reaction into ice water and extracting with ether. The combined ether layers are washed with water until neutral and with brine and dried over calcium sulfate. After filtration the ether is distilled off to give a mixture of 1-bromo-2-fluoro-2-butene and 3-bromo-2-fluoro-1-butene.

The above mixture of 1-bromo-2-fluoro-2-butene and 3-bromo-2-fluoro-1-butene is reacted with ethyl N-(4-hydroxyphenoxyethyl)carbamate, following the procedures of Example 4 to yield, following separation by prep. TLC, ethyl N-{2-[4-(2-fluoro-1-methyl-2-propenoxy)propenoxy)phenoxy]ethyl}carbamate (compound 78, Table A) and ethyl N-{2-[4-(2-fluoro-2-butenoxy)phenoxy]ethyl}carbamate (compound 79, Table A).

EXAMPLE 26

To NaH (0.246 g, 10.2 mmol) in 10 ml of DMF at 20° is added 4-(3-methyl-2-butenoxy)phenol (1.33 g, 10.2 mmol) in 5 ml of DMF. After anion formation is complete, the reaction is cooled to 5° C. and 2-chloropropionitrile (10.095 g, 12.2 mmol) is added gradually. Then, the reaction mixture is warmed to RT and heated at 45° for 18 hrs. The reaction is cooled to RT, poured into ice water and extracted with ether. The combined organic layers are washed with 10% NaOH, followed with water until neutral, and with brine, and dried over calcium sulfate. Ether is removed under vacuum to give 2-[4-(3-methyl-2-butenoxy)phenoxy]-propionitrile.

To 2-[4-(3-methyl-2-butenoxy)phenoxy]propionitrile (2.0 g, 8.6 mmol) in 20 ml of ether is added lithium aluminum hydride (0.328 g, 8.6 mmol) in portions at 5°. After the addition, the reaction mixture is slowly warmed to RT and stirred for 18 hours. The reaction is worked up by cooling to 5° and by adding 0.33 ml of water, followed by 0.33 ml of 15% NaOH and 1 ml of water, with vigorous stirring. The solid is filtered off and the filtrate is washed with brine and dried over calcium sulfate. The ether is removed to give 2-[4-(3-methyl-2-butenoxy)phenoxy)phenoxyl]propylamine.

Following the procedure of Example 8, the above substituted propylamine (2.0 g, 8.5 mmol) and ethyl chloroformate (1.01 g, 9.35 mmol) are reacted together, in the presence of pyridine (0.74 g, 9.35 mmol), to give ethyl N-{2-[4-(3-methyl-2-butenoxy)phenoxy]-propyl} carbamate, MS m/e 307 (M+).

nmr (CDCl$_3$) δ 1.23 (m, 6H, O—CH$_2$—CH$_3$ and O—CH(CH$_3$)—CH$_2$), 1.77 (m, 6H, vinyl methyl groups), 3.37 (m, 2H, CH$_2$—NH), 4.13 (q, 2H, J=7 Hz, O—CH$_2$—CH$_3$), 4.47 (m, 2H, C=CH—CH$_2$—O), 5.10 (bs, 1H, NH), 5.49 (m, 1H, vinyl proton), and 6.83 ppm (s, 4H, aromatic protons).

EXAMPLE 27

To a solution of 4-(1-methylpropoxy)phenol (1.58 g, 9.5 mmol) in 10 ml of DMF at 50° is added potassium carbonate (3.90 g, 28.0 mmol). To this is added dropwise methyl 2-bromopropionate (3.2 ml, 30.0 mmol) in 10 ml of DMF. The mixture is stirred at 70° for 60 hours. The cooled reaction is worked up by addition of water and extraction with a mixture of ether/hexane (3X). The combined organic extracts are washed with 10% sulfuric acid, with water and with brine, dried and the solvent removed to give methyl 2-[4-(1-methylpropoxy)phenoxy]-propanate.

To the above propanoate (2.52 g, 7.4 mmol) in 25 ml of methanol at 0° is added 10 ml of conc. ammonium hydroxide. The reaction mixture is allowed to warm to RT and is stirred at RT overnight. The methanol is removed by rotoevaporation and the aqueous portion is filtered to give methyl 2-[4-(1-methylpropoxy)phenoxy]propanamide, a white solid.

To the above propanamide (1.32 g, 5.6 mmol) in 10 ml of THF at 0° is added dropwise 0.97 M BH$_3$-THF (35 ml) over 40 min. The solution is heated under reflux overnight and is then allowed to sit at RT for 48 hours, after which 10 ml of water is added dropwise over 30 min., followed by dropwise addition of 20 ml of aqueous 5N HCl. The THF is removed by distillation, and the aqueous phase is saturated with NaOH pellets and extracted with ether (3X). The combined organic layers are washed with water and with brine, dried and solvent removed to give 2-[4-(1-methylpropoxy)phenoxy]propylamine.

Following the procedure of Example 20, the above substituted propylamine (1.13 g, 5.1 mmol) and ethyl chloroformate (10.6 mmol) are reacted together in the presence of 10% NaOH (3.54 ml), to give ethyl N-{2-[4-(1-methylpropoxy)phenoxy]propyl}carbamate, MS m/e 296 (M+ +H), (compound 1, Table B).

nmr $^{13}$C (CDCl$_3$) 156.68 (C=O), (1.52.46, 151,37, 117.13-aromatic), 75.69 (CH$_2$—CH(CH$_3$)—O), 73.63 (O—CH(CH$_3$)—CH$_2$—NH), 60.52 (COO—CH$_2$—CH$_3$), 45.73 (CH—CH$_2$—NH), 28.94 (O—CH(CH$_3$)—CH$_2$NH), 19.03 (CH$_3$—CH$_2$—CH), 17.02 (CH$_3$—CH$_2$—CH), 14.37 (O—CH$_2$—CH$_3$), 9.55 (CH$_3$—CH$_2$—CH(CH$_3$)).

EXAMPLE 28

To a solution of ethyl N-[4-(1-methylpropylthio)-phenoxyethyl]carbamate (cpd. 40, from Example 13) (2.13 g, 7.1 mmol) in 7 ml of methanol at 0° is added, dropwise over 5 min., sodium metaperiodate (1.67 g, 7.8 mmol) in 13 ml of water. The mixture is stirred for 3 hours while warming to RT. The reaction is worked up by addition of water and extraction of ether. The combined organic extracts are washed with saturated sodium thiosulfate, with water and with brine, dried and the solvent is removed to give ethyl N-{2-[4-(1-methylpropylsulfinyl)phenoxy]-ethyl}carbamate (compound 80, Table A).

Ethyl N-{2-[4-(1-methylpropylthiophenoxy]ethyl} carbamate (2.12 g, 7.1 mmol) is reacted with two equivalents of m-chloroperbenzoic acid in chloroform to yield N-{2-[4-(1-methylpropylsulfonyl)phenoxy]ethyl} carbamate (compound 81, Table A). Alternatively, either hydrogen peroxide in warm acetic acid or excess hydrogen peroxide with selenium dioxide in methanol is used as the oxidant.

EXAMPLE 29

Following the procedure of Example 1, each of 2-fluoro-4-(1-methylpropoxy)phenol, 5-methyl-4-(1-methylpropoxy)phenol, 3-chloro-4-(1-methylpropoxy)-phenol, 2-trifluoromethyl-4-(1-methylpropoxy)phenol, 2-fluoro-4-(3-methyl-2-butenoxy)phenol and 3-methyl-4-(3-methyl-2-butenoxy)phenol is reacted with ethyl 2-chloroethylcarbamate to yield, respectively, ethyl N-{2-[2-fluoro-4-(1-methylpropoxy)phenoxy]ethyl}carbamate, ethyl N-{2-[5-methyl-4-(1-methylpropoxy)phenoxy]ethyl}carbamate.

ethyl N-{2-[3-chloro-4-(1-methylpropoxy)phenoxy]ethyl}carbamate.

ethyl N-{2-[2-trifluoromethyl-4-(1-methylpropoxy)-phenoxy]ethyl}carbamate.

ethyl N-{2-[2-fluoro-4-(3-methyl-2-butenoxy)phenoxy]ethyl }-carbamate, and ethyl N-{2-[3-methyl-4-(3-methyl-2-butenoxy)-phenoxy]ethyl }-carbamate.

EXAMPLE 30

Following the procedure of Example 1, 4-(1-methylpropoxy)-phenol is reacted with each of methyl 2-chloroethylcarbamate, isopropyl 2-chloroethylcarbamate, 4-chlorophenyl 2-chloroethylcarbamate and 2-propenyl 2-chloroethylcarbamate to give, respectively, methyl N-{2-[4-(1-methylpropoxy)phenoxy]ethyl }carbamate, isopropyl N-{2-[4-(1-methylpropoxy)phenoxy]ethyl}carbamate, 4-chlorophenyl N-{2-[4-(1-methylpropoxy)phenoxy]ethyl}carbamate, and 2propenyl N-{2-[4-(1-methylpropoxy)phenoxy]ethyl}carbamate, (compounds 2, 3, 4 and 5, respectively, under Table B).

EXAMPLE 31

To a mixture of (S)-(+)-2-butanol (9.73 g, 131.3 mmol) and triethylamine (17.75 g, 175.0 mmol) in 250 ml of methylene chloride at −10° is added dropwise methanesulfonyl chloride (18.55 g, 162.0 mmol). After addition is complete, the reaction mixture is held at −10° for 15 min. The reaction is then quenched by addition of ice water and the phases separated. The organic phase is washed with cold 1N sulfuric acid, with saturated sodium bicarbamate and with brine, filtered, dried and stripped in vacuo below 25° to give (S)-(+)-2-butylmethanesulfonate.

A mixture of methyl 4-hydroxyphenoxyacetate (25.50 g, 140.0 mmol) and potassium carbonate (18.67 g, 135.0 mmol) in 70 ml of DMF is heated to 75°, with stirring, for 40 min. The above methanesulfonate (10.66 g, 70.0 mmol) in 5 ml of DMF is added slowly over 5 min. The reaction mixture is allowed to stand at 60° overnight. To the cooled reaction mixture is added ice water, followed by cold sulfuric acid to bring it to pH 4-5. Additional water is added and the mixture is extracted with ether (3X). The combined ether extracts are washed with 1% sulfuric acid/1% potassium dihydrophosphate, with 1% potassium dihydrophosphate (2X), then hexane is added and the organic layer is washed with 10% sodium hydroxide (5X), with water and with brine; dried; filtered and the filtrate evaporated to give methyl (R)-(−)-4-(1-methylpropoxy)-phenoxyacetate, $[\alpha]_D^{20} - 20.67$.

A mixture of the above ester (2.50 g), methanol (20 ml) and 5 ml of 10% NaOH is stirred at RT for 24 hours. The reaction is then worked up by addition of water and 10% sulfuric acid to adjust the pH to 3 and extraction with ether. The combined organic layers are washed with water and with brine, dried, filtered and the filtrate stripped to give (R)-(−)-4-(1-methylpropoxy)phenoxyacetic acid, $[\alpha]_D^{20} - 21.369°$.

To the above acid (2.07 g, 9.23 mmol) in 10 ml of THF at 5° under $N_2$ with stirring is added borane/THF (25 ml) over a period of 20 min. The mixture is heated under reflux for 45 min., then cooled to 5° and water is added until gas evolution ceases, followed by addition of 10% NaOH (10 ml). A two-phase system results; the upper, organic phase is isolated and concentrated in vacuo to remove most of the THF. The lower, aqueous phase is extracted with ether (2X). the ether extracts and the concentrate are combined, washed with water and brine, dried, filtered, the filtrate is concentrated in vacuo and the residue is purified by distillation at reduced pressure to give (R)-2-[4-(1-methylpropoxy)-phenoxy]ethanol, $[\alpha]_D^{20} - 23,332°$.

Following the procedure of Example 9, the above alcohol (0.42 g, 2.0 mmol) is reacted with ethyl isocyanate (0.18 ml, 2.2 mmol) to give O-2-[(R)-4-(1-methylpropoxy)phenoxy]ethyl N-ethylcarbamate, specific rotation $[\alpha]_D^{20} = -19.103°$ (c=10% in methanol).

In an analogous manner, (R)-(−)-2-butanol is converted to O-2-[(S)-4-(1-methylpropoxy)phenoxy]ethyl N-ethylcarbamate, specific rotation $[\alpha]_D^{23} = +19.78°$.

EXAMPLE 32

To prewashed sodium hydride (1.01 g, 42.0 mmol) in 60 ml of DMF at 20° is added 4-(1-methylpropoxy)-phenol (7.0 g, 42.0 mmol) in 5 ml of DMF over 30 min. After 1 hour at RT, chloroacetonitrile (3.80 g, 50.4 mmol) in 5 ml of DMF is added dropwise to the mixture at 5°-8° over 15 min. After addition, the reaction is warmed slowly to RT and stirred at RT for 18 hours. The mixture is then poured into ice water and ether and extracted with ether (3X). The combined organic phases are washed with 10% NaOH, with water until neutral and with brine, dried, filtered and solvent removed in vacuo to give 4-(1-methylpropoxy)phenoxyacetonitrile.

To the above phenoxyacetonitrile (7.21 g, 35.2 mmol) in 60 ml of THF at 8° is added 1M diborane (61.50 g, 61.5 mmol) over 45 min. The reaction is warmed to RT and stirred for 6 hours. The reaction is stirred for 16 hours. The THF-$H_2O$ is removed in vacuo and water and ether are added to the while sold, followed by 10% aqueous sodium hydroxide to basify. The product is extracted with ether (3X) and the combined organic phases are washed with water and with brine, dried, filtered and solvent removed to give 2-[4-(1-methylpropoxy)phenoxy]ethylamine.

To the above ethylamine (0.75 g, 3.6 mmol) and pyridine (0.63 g, 7.9 mmol) in 8 ml of ether at 5° is added propyl chloroformate (0.48 g, 3.9 mmol) over 5 min. The reaction is stirred at 5° for 1 hour and at RT for 2 hours. Excess chloroformate is quenched and the mixture is stirred for 2 hours. The mixture is poured into water and ether and the product is extracted with ether (3X). The combined ether layers are washed with 2N sulfuric acid, with 10% sodium carbonate, with water and with brine, dried, filtered and solvent removed to give, propyl N-{2-[4-(1-methylpropoxy)-phenoxyl]ethyl}carbamate, MS (m/e) 295 (M+) (compound 6, Table B).

EXAMPLE 33

To a solution of methyl 4-(1-methylpropoxy)phenoxyacetate (7.94 g, 33.3 mmol) in 65 ml of dry DMF at 0° and with stirring is added methylamine gas to saturation (ca. 25 min.). A trace of sodium methoxide (ca. 10 mg) is added and the mixture is allowed to warm to RT. After 20 hour at RT, the reaction mixture is poured into ice water and 10 ml of 3N sulfuric acid and extracted with ether. The combined organic phases are washed with water, with 10% sodium bicarbonate, with water and with brine, dried, filtered and the filtrate evaporated in vacuo to give 4-(1-methylpropoxy)-N-methylacetamide.

To a solution of the above acetamide (6.63 g, 27.9 mmol) in 18 ml of THF at 25° and with stirring is slowly added 10 ml of 1 M diborane in THF over 40 min. The reaction mixture is heated at reflux for 19 hours, after which it is cooled to 0° and water is added dropwise followed by 6 N HCl. The solvent is distilled off and the residue is cooled to 0°. It is poured into water, washed with ether (3X) and with water and conc. HCl. The aqueous phases are combined and cooled to 0°, and a 50% solution of NaOH is added until the mixture is just strongly basic. The mixture is extracted with ether (3X) and the combined ether extracts are washed with brine, dried and filtered and the filtrate is concentrated in vacuo to give N-methyl-N-2-[4-(1-methylpropoxy)-ethylamine.

To a solution of the above substituted ethylamine (1.34 g, 6.0 mmol) in 20 ml of dry ethyl ether is slowly added ethyl chloroformate (0.316 ml). 1.234 Ml of 10% aqueous NaOH and 0.158 ml of ethyl chloroformate are then added simultaneously, followed by a second addition in the same proportions. After 30 min., the mixture is added to water and extracted with ether. The combined organic phases are washed with 3 N sulfuric acid, with water and with brine, dried and filtered and the filtrate concentrated in vacuo to give N-methyl-N-2-[4-(1-methylpropoxy)phenoxy]ethyl O-ethylcarbamate (compound 82, Table A).

EXAMPLE 34

Following the procedure of Example 9, 2[4-(3-methyl-2-butenoxy)phenoxy]ethanol and isopropyl isopropyl isocyanate are reacted together to give O-2-[4-(3-methyl-2-butenoxy)phenoxy]ethyl N-isopropylcarbamate, MS, m/e 307 (M+).

nmr (CDCl$_3$) δ 1.15 (d, 6H, J=6 Hz, OCH(CH$_3$)$_2$), 1.77 (m, 6H, vinyl methyl groups), 5.50 (m, 1H, vinyl proton) and 6.85 ppm (s, 4H, aromatic protons).

In the same way, each of the isocyanates or isothiocyanates under column V is reacted with 2-[4-(1-methylpropoxy)phenoxy]-ethanol to give the corresponding carbamate under Table B (compounds 7-12).

V 7. isopropyl isocyanate
8. 2-chloroethyl isocyanate
9. tert-butyl isocyanate
10. 1-propenyl isocyanate
11. n-propyl isothiocyanate
12. isopropyl isothiocyanate Following the same procedures, 2-[4-(1-methylpropoxy)-phenoxy]propanol and ethyl isocyanate are reacted together to give compound 13 (Table B).

Likewise, 2-[4-(1-methylpropylthio)phenoxy]ethanol is reacted with isopropyl isocyanate to give compound 14 in Table B. Also, 2-[4-(1-methylpropylthio)phenoxy]propanol is reacted with each of ethyl isocyanate and ethyl isothiocyanate to give the corresponding compounds 15 and 16 in Table B.

In the same way, each of 2-[4-(1-methylpropoxy)-phenoxy]-ethylthiol and 2-[4-(1-methylpropylthio)-phenoxy]ethylthiol is reacted with ethyl isocyanate to give the corresponding carbamate (compounds 87 and 88, Table A).

EXAMPLE 35

To a mixture of sodium hydride (0.12 g) in 5 ml of DMF, cooled in an ice bath, is slowly added 2-[4-(1-methylpropoxy)-phenoxy]ethanol (0.50 g). The mixture is stirred at RT for 1 hour, after which diethylcarbamoyl chloride (0.50 g) is added. The reaction mixture is stirred at RT for 24 hours, then poured into water and extracted with ether. The combined organic layers are washed with water and dried and the solvent is evaporated off to give, following purification by prep. TLC, 2-[4-(1-methylpropoxy)phenoxy]ethyl N,N-diethylcarbamate (compound 17, Table B).

nmr (CDCl$_3$) δ 0.8-1.8 (m, 14H), 3.2 (q, bH), 3.4-4.5 (m, 5H) and 6.8 ppm (s, 4H).

Following the above procedures, each of dimethylthiocarbamoyl chloride, diethylthiocarbamoyl chloride and diisopropylcarbamoyl chloride is reacted with the sodium salt of 2-[4-(1-methylpropoxy)phenoxy]ethanol to give the corresponding carbamate under Table B (compounds 18, 19 and 20, respectively).

EXAMPLE 36

A mixture of 2-[4-(1-methylpropoxy)phenoxy]ethanol (1.26 g), 1,1'-carbonyldiimidazole (0.97 g) and a trace amount of sodium imidazolide in 25 ml of THF is stirred at 30° for 2 hours. Sec-butylamine (0.46 g) in 5 ml of THF is added, and the resulting mixture is stirred at 60° for 48 hours, after which it is concentrated in vacuo. The resulting solid is taken up in water, neutralized to pH 7.8 and extracted with ether. The combined organic phases are washed with water and with brine, dried and concentrated to give, following purification by column chromatography, 2-[4-(1-methylpropoxy)phenoxy]ethyl N-1-methylpropylcarbamate (compound 21, Table B).

nmr (CDCl$_3$) δ 0.8-1.8 (m, 16H), 3.4-3.8 (m, 1H), 4.0-4.4 (m, 5H), 4.7 (b, 1H) and 6.8 ppm (s, 4H).

Following the above procedures, 2-[4-(1-methylpropoxy)-phenoxy]ethanol and cyclopropylamine are reacted together to give 2[4-(1-methylpropoxy)phenoxy]ethyl N-cyclopropylcarbamate (compound 22, Table B).

nmr (CDCl$_3$) δ 0.4-0.7 (m, 4H), 0.8-1.1 (t, 3H), 1.1-1.3 (d, 3H), 1.3-1.9 (m, 2H), 2.5 (b, 1H), 3.9-4.4 (m, 5H), 5.4 (b, 1H) and 6.8 ppm (s, 4H).

EXAMPLE 37

Following the procedure of Example 8, 13 and 20, 2-[4-(1-methylpropoxy)phenoxy]ethylamine is reacted with each of the chloroformates or chlorothioformates under column VI to give the corresponding carbamates, compounds 23, 24, 25 and 26 in Table B.

In the same manner, 2-[4-(1-methylpropoxy)phenoxy]-2-methylethylamine is reacted with each of the chloroformates or chlorothioformates under column VI to give the corresponding carbamates, compounds 27, 28, 29 and 30 in Table B.

VI isopropyl chloroformate
S-isopropyl chlorothioformate
S-ethyl chlorothioformate
sec-butyl chloroformate Following the same procedures, 2-[4-(1-methylpropylthio)phenoxy]-2-methylethylamine is reacted with each of S-ethyl chlorothioformate and ethyl chloroformate to give, respectively, compounds 31 and 32 under Table B.

EXAMPLE 38

Following the procedures of Example 1, isopropyl 2-chloroethylcarbamate is prepared and is then reacted with 4-(3-methyl-2-butenoxy)phenol to give isopropyl N-{2-[4-(3-methyl-2-butenoxy)phenoxy]ethyl}carbamate, MS m/e 307 (M+).

nmr (CDDl$_3$) δ 1.20 (d, 6H, J=6Hz, CH(CH$_3$)$_2$), 1.74 (m, 6H, vinyl methyl groups), 3.51 (m, 2H, CH$_2$—N), 3.97 (m, 2H, CH$_2$—CH$_2$—NH), 4.44 (m, 2H, C=CH—CH$_2$—O), 5.47 (m, 1H, vinyl proton) and 6.82 ppm (s, 4H, aromatic protons).

EXAMPLE 39

To a solution of 4.04 g (10.0 mmol) of Lawesson's reagent [2,4-bis(4-methoxyphenyl)-1,3-diatha-2,4-diphosphetane-2,4disulfide] in 100 ml of toluene under reflux is added ethyl N-2-[4-(1methylpropoxy)phenoxylethyl carbamate (2.81 g, 10.0 mmol) in 10 ml of toluene. The reaction mixture is heated under reflux overnight, after which it is allowed to cool to RT and then poured into water. The resulting organic phase is washed with 5% sodium bicarboante, with 10% sulfuric acid, with water and with brine, dried and filtered. The solvent is removed by rotoevaporation to give a solid which is rinsed with acetone. The acetone is evaporated off, and the resulting brown oil is purified by column chromatography to give O-ethyl N-{2-[4-(1-methylpropoxy)phenoxy]-ethyl}thiocarbamate (compound 33, Table B).

nmr $^{13}$C (CDCl$_3$) 190.65 (C=S), 152.57–115.35 (aromatic), 76.02 (CH$_2$—CH(CH$_3$)—O), 66.27 (O—CH$_2$—CH$_2$—NH), 44.54 (O—CH$_2$—CH$_3$), 42.28 (O—CH$_2$—CH$_2$—NH), 29.05 (CH$_3$—CH$_2$—CH(CH$_3$)), 19.19 (CH$_3$—CH$_2$—CH(CH$_3$)), 14.15 O—CH$_2$—CH$_3$), 9.71 (CH$_3$—CH$_2$—CH(CH$_3$)).

EXAMPLE 40

A mixture of pre-washed sodium hydride (0.71 g) and 4-(2-methyl-1-oxobutyl)phenol (2.50 g) in 25 ml of THF is stirred at RT for 1 hour, after which the THF is removed by rotoevaporation. The DMF is added to the resulting sodium salt, followed by slow addition of ethyl 2-chloroethylcarbamate (2.33 g) in 10 ml of DMF. The mixture is stirred at 80°–85° for 6 hours, then poured into water and extracted with ether. The combined organic extracts are washed with water and with brine, dried and the solvent removed by evaporation to give, after purification by column chromatography, ethyl N-{2-[4-(2-methyl-1-oxobutyl) phenoxy]ethyl}carbamate (compound 34, Table B).

nmr CDCl$_3$) δ 0.8–1.9 (m, 11H), 3.2–3.8 (m, 3H(), 4.0–4.4 (m, 4H), 7.0 (d, 2H), and 8.0 ppm (d, 2H).

EXAMPLE 41

To a mixture of 2-butanone (5 ml), 2-(4-aminophenoxy)ethyl N-ethylcarbamate (1.00 g) and sodium acetate (2.50 g) in a solution of 5 ml of acetic acid and 10 ml of water, cooled to −5°, is added sodium borohydride (4.00 g) in portions. After addition is complete, the reaction mixture is adjusted to alkaline pH and is extracted with ether. The combined organic extracts are concentrated and the crude product is purified by column chromatography to give 2-[4-(1-methylpropylamino)phenoxy]ethyl N-ethylcarbamate (compound 35, Table B).

nmr (CDCl$_3$) δ 0.8–2.8 (m, 11H), 2.9–3.5 (m, 3H), 3.9–4.4 (m 4H), 5.1. (b, 1H) and 6.8 ppm (s, 4H).

EXAMPLE 42

Following procedure C in H. Tilles, JACS 81:714 (1959) a solution of dimethylamine (0.58 ml, 8.79 mmol) and triethylamine (1.22 ml, 8.79 mmol) in 3ml of t-butyl alcohol is cooled to 15°, after which carbonylsulfide (0.71 g, 11.87 mmol) is passed in which vigorous stirring. The solution is then warmed to 30°, with stirring, 2-[4-(1-methylpropoxy)phenoxy]ethyl bromide (2.40 g, 8.79 mmol) is added rapidly. The reaction mixture is heated slowly to 50° and maintained at 50° for 3 hours. The solvent is then distilled off and the product is worked up to give S-2-[4-(1-methylpropoxy)phenoxy]ethyl N,N-dimethylthiocarbamate (compound 36, Table B).

nmr (CDCl$_3$) δ 0.97 (m, 3H, J=6Hz, CH$_3$CH$_2$CH(CH$_3$)), 1.23 (d, 3H, J=6 Hz, CH$_3$CH$_2$CH(CH$_3$)), 3.00 (s, 6H, N(CH$_3$)$_2$), 3.28 (t, 3H, J=6 Hz, CGH$_2$S), 4.13 (t, 2H, J=6 Hz, OCH$_2$) and 6.84 ppm (s, 4H, aromatic protons).

In the same way S-2-[4-(1-methylpropoxy)phenoxy]ethyl N-ethyl-N-methylthiocarbamate is prepared from methylethylamine, carbonyl sulfide, triethylamine and 2-[4-(1-methylpropoxy)phenoxy]ethyl bromide (compound 37, Table B).

nmr (CDCl$_3$) δ 0.97 (m, 3H, J=6.5 Hz, CH$_3$CH$_2$CH(CH$_3$)), 1.17 (t, 3H, J=6 Hz, NCH$_2$CH$_3$), 1.25 (d, 3H, J=6 Hz, CH$_3$CH$_2$CH(CH$_3$)), 3.00 (s, 3H, NCH$_3$), 3.37 (m, 2H, NCH$_2$CH$_3$), 4.13 (t, 2H, J=6 Hz, OCH$_2$) and 6.84 ppm (s, 4H, aromatic protons).

Example 43

To sodium hydride (1.35 g, 56.2 mmol), prewashed in hexane, in 30 ml of DMF is added 4-nitrophenol in 5 ml of DMF at 15°. After anion formation is complete, ethyl N-chloroethylcarbamate (7.12 g, 47.0 mmol) is slowly added. The slurry is heated to 85° and stirred for 17 hours, after which the reaction is cooled to RT, poured into ice water and ether, and extracted with ether. The combined organic layers are washed with 10% sodium hydroxide, with water and with brine, dried and filtered and the solvent is removed by rotoevaporation to give ethyl N-[2-(4-nitrophenoxy)-ethyl]carbamate.

To the above phenoxy-substituted carbamate (5.52 g, 21.7 mmol) suspended in 110 ml of ethanol at 22° is added ammonium chloride (11.6 g, 217.0 mmol) in 60 ml of water. The slurry is warmed to 70° and iron dust (6.0 g, 108.5 mmol) is added gradually over 1 hour. The resulting slurry is cooled to 22°, celite is added, and the reaction is filtered. The filtrate is concentrated by rotoevaporation and water and ether are added. The product is extracted into ether and the combined organic layers are washed with water and with brine, dried and filtered and the solvent is removed to give ethyl N-[2-(4-aminophenoxy)ethyl]carbamate.

To ethyl N-[2-(4-aminophenoxy)ethyl]carbamate (1.50 g, 6.7 mmol) and pyridine (1.10 ml, 13.4 mmol) in 10 ml of THF at 22° is slowly added 1-bromo-3-methyl-2-butene. The reaction is stirred at 22° for 18 hours, after which it is poured into water and extracted with ether. The combined organic layers are washed with water and with brine, dried and filtered and the solvent is removed to give a mixture of the monoalkylated and dialkylated products, which are separated by chromatography:

ethyl N-2[4-(3-methyl-2-butenylamino)phenoxy]ethyl carbamate, MS m/e 293 (M+) +H); nmr (CDCl$_3$) 1.23 (t, 3H, J=7 Hz, OCH$_2$CH$_3$), 1.72 (bs, 6H, vinyl methyl groups), 4.13 (q, 2H, J=7 Hz, OCH$_2$CH$_3$), 5.27 (m, 2H, vinyl proton and NH—C(O)) and 6.68 ppm (m, 4H, aromatic protons); and ethyl N-2-[4-((bis(3-methyl-2butenyl)amino))phenoxy]-ethyl carbamate, MS m/e 361 (M++H); nmr (CDCl$_3$) 1.24 (t, 3H, J=7 Hz, OCH$_2$CH$_3$), 1.68 (bs, 12H, vinyl methyl groups), 4.13 (q, 2H, J=7 Hz, OCH$_2$CH$_3$), 5.20 (m, 3H, vinyl protons and NH) and 6.73 ppm (s, 4H, aromatic protons).

EXAMPLE 44

Bis-{5-(2-N-ethylcarbamoyloxyethoxy)phenyl} disulfide (2.40 g) and diphenylphosphine polystyrene (2.50 g) are dissolved in a solution of 20 ml of THF, 5 ml of water and 5 drops of conc. HCl, and stirred at RT for 22 hours. 1-Bromo-3-methyl-2-butene (1.64 g). and triethylamine (1.18 g) are added and the resulting mixture is stirred at RT to 25 hours. The reaction is filtered to remove the polystyrene resin, poured into water and extracted with ether. The combined organic layers are washed with water, dried and evaporated, and the residue is purified by column chromatography to give O-2-[4-(3-methyl-2-butenylthio)phenoxy]ethyl N-ethylcarbamate (compound 42, Table A).

TABLE A $$R-W^1-\underset{}{\underset{}{\bigcirc}}-W-CH_2-CH_2-X-\overset{Y}{\underset{\|}{C}}-X^1-CH_2CH_3$$

| Cpd | R | $W^1$ | W | X | Y | $X^1$ | m/s (M$^+$) |
|---|---|---|---|---|---|---|---|
| 1 | CH$_3$—C(CH$_3$)=CH—CH$_2$ | O | O | NH | O | O | 293 |
| 2 | CH$_3$—CH(CH$_3$) | O | O | NH | O | O | 267 |
| 3 | CH≡C—CH$_2$ | O | O | NH | O | O | 263 |
| 4 | CH≡C—CH$_2$—CH$_2$—CH$_2$ | O | O | NH | O | O | 291 |
| 5 | Cl—CH=CH—CH$_2$ | O | O | NH | O | O | 299 |
| 6 | CH$_2$=C(CH$_3$)—CH$_2$ | O | O | NH | O | O | 279 |
| 7 | CH$_3$—C(CF$_3$)=CH—CH$_2$ | O | O | NH | O | O | 347 |
| 8 | CH$_3$—C(CH$_3$)=CH—CH$_2$—CH$_2$ | O | O | NH | O | O | 307 |
| 9 | CH$_3$—C(Cl)=CH—CH$_2$ | O | O | NH | O | O | 277 |
| 10 | CH$_2$=CH—CH$_2$—CH$_2$—CH$_2$ | O | O | NH | O | O | 293 |
| 11 | CH$_3$—CH$_2$—O—CH$_2$ | O | O | NH | O | O | 283 |
| 12 | CH$_3$—O—C(CH$_3$)(CH$_3$)—CH$_2$—CH$_2$ | O | O | NH | O | O | 325 |
| 13 | CH$_3$—CH$_2$—CH(CH$_3$) | O | O | NH | O | O | 281 |
| 14 | CH$_3$—CH$_2$—CH$_2$—CH(CH$_3$) | O | O | NH | O | O | 296* |
| 15 | Cl—CH$_2$—CH$_2$—CH$_2$ | O | O | NH | O | O | 301 |
| 16 | Cl—C(Cl)=CH—CH$_2$ | O | O | NH | O | O | 334 |
| 17 | CH$_3$—CH$_2$—CH(CH$_3$—CH$_2$) | O | O | NH | O | O | 295 |
| 18 | CH$_3$—CH=CH—CH(CH$_3$) | O | O | NH | O | O | 294* |
| 19 | CH$_3$—CH(CH$_3$)—CH$_2$—CH(CH$_3$) | O | O | NH | O | O | 309 |
| 20 | CH$_3$—CH$_2$—CH(CH$_3$)—CH$_2$ | O | O | NH | O | O | 295 |

TABLE A-continued $$R-W^1-\text{C}_6\text{H}_4-W-CH_2-CH_2-X-\overset{\overset{Y}{\|}}{C}-X^1-CH_2CH_3$$

| Cpd | R | W¹ | W | X | Y | X¹ | m/s (M⁺) |
|---|---|---|---|---|---|---|---|
| 21 | CH₃—CH₂—CH₂—CH₂—CH(CH₃)— | O | O | NH | O | O | 310* |
| 22 | Cl—C≡C—CH₂— | O | O | NH | O | O | 297 |
| 23 | CH₃—C(CH₃)=CH—CH(CH₃)— | O | O | NH | O | O | 307 |
| 24 | CH₃—CH₂—C(CH₃)=CH—CH₂— | O | O | NH | O | O | 307 |
| 25 | CH₂=C(Cl)—CH₂— | O | O | NH | O | O | 299 |
| 26 | cyclobutyl (CH₂—CH, CH₂—CH₂) | O | O | NH | O | O | 279 |
| 27 | CH₃—C(CH₃)(epoxide)—CH—CH₂ | O | O | NH | O | O | 309 |
| 28 | CF₃—CH₂— | O | O | NH | O | O | 307 |
| 29 | CH₃—CH(CF₃)— | O | O | NH | O | O | 339** |
| 30 | CH₃—CH₂—CH(CH₃)— | O | O | O | O | NH | 281 |
| 31 | CH₃—C(CH₃)=CH—CH₂— | O | O | O | O | NH | 293 |
| 32 | CH₃—CH₂—CH₂—CH(CH₃)— | O | O | O | O | NH | |
| 33 | CH₃—CH₂—CH(CH₃)—CH₂— | O | O | O | O | NH | |
| 34 | CH₂=C(Cl)—CH₂— | O | O | O | O | NH | |
| 35 | CH₃—CH₂—CH₂—CH₂—CH(CH₃)— | O | O | O | O | NH | |
| 36 | CH₃—CH₂—CH(CH₃)— | O | O | O | S | NH | 298* |
| 37 | CH₃—C(CH₃)=CH—CH₂— | O | O | O | S | NH | |
| 38 | CH₃—CH₂—CH(CH₃)— | S | O | O | S | NH | 314* |

TABLE A-continued

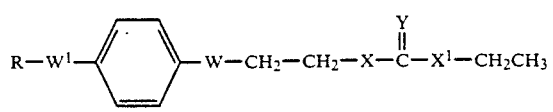

| Cpd | R | W¹ | W | X | Y | X¹ | m/s (M⁺) |
|---|---|---|---|---|---|---|---|
| 39 | CH₃—CH₂—CH(CH₃) | S | O | O | O | NH | 297 |
| 40 | CH₃—CH₂—CH(CH₃) | S | O | NH | O | O | 297 |
| 41 | CH₃—C(CH₃)=CH—CH₂ | S | O | O | S | NH | |
| 42 | CH₃—C(CH₃)=CH—CH₂ | S | O | O | O | NH | 309 |
| 43 | CH₃—C(CH₃)=CH—CH₂ | S | O | NH | O | O | 309 |
| 44 | CH₃—CH₂—CH(CH₃) | S | S | NH | O | O | 313 |
| 45 | CH₃—CH₂—CH(CH₃) | S | S | NH | O | S | 330* |
| 46 | CH₃—C(CH₃)=CH—CH₂ | S | S | NH | O | O | |
| 47 | CH₃—C(CH₃)=CH—CH₂ | S | S | NH | O | S | |
| 48 | CH₃—CH₂—CH(CH₃) | O | O | NH | O | S | 314* |
| 49 | CH₃—C(CH₃)=CH—CH₂ | O | O | NH | O | S | |
| 50 | CH₃—CH₂—CH(CH₃) | S | S | NH | S | NH | 328 |
| 51 | CH₃—CH₂—CH(CH₃) | O | O | NH | S | NH | |
| 52 | CH₃—C(CH₃)=CH—CH₂ | S | S | NH | S | NH | |
| 53 | CH₃—C(CH₃)=CH—CH₂ | O | O | NH | S | NH | |
| 54 | CH₃—CH₂—CH(CH₃) | S | S | NH | O | NH | 313* |
| 55 | CH₃—CH₂—CH(CH₃) | O | O | NH | O | NH | |

TABLE A-continued $$R-W^1-\phenyl-W-CH_2-CH_2-X-\overset{Y}{\underset{\|}{C}}-X^1-CH_2CH_3$$

| Cpd | R | W¹ | W | X | Y | X¹ | m/s (M⁺) |
|---|---|---|---|---|---|---|---|
| 56 | CH₃—C(CH₃)=CH—CH₂ | S | S | NH | O | NH | |
| 57 | CH₃—C(CH₃)=CH—CH₂ | O | O | NH | O | NH | |
| 58 | CH₃—CH₂—CH(CH₃) | S | S | O | O | O | 314 |
| 59 | CH₃—CH₂—CH(CH₃) | S | O | O | O | O | 298 |
| 60 | CH₃—CH₂—CH(CH₃) | O | O | O | O | O | 282 |
| 61 | CH₃—C(CH₃)=CH—CH₂ | S | S | O | O | O | |
| 62 | CH₃—C(CH₃)=CH—CH₂ | S | O | O | O | O | |
| 63 | CH₃—C(CH₃)=CH—CH₂ | O | O | O | O | O | |
| 64 | CH₃—CH₂—CH(CH₃) | S | S | O | O | S | 330 |
| 65 | CH₃—CH₂—CH(CH₃) | O | O | O | O | S | 298 |
| 66 | CH₃—C(CH₃)=CH—CH₂ | S | S | O | O | S | |
| 67 | CH₃—C(CH₃)=CH—CH₂ | O | O | O | O | S | |
| 68 | CH₃—CH₂—CH(CH₃) | S | S | NH | S | S | 346* |
| 69 | CH₃—CH₂—CH(CH₃) | O | O | NH | S | S | |
| 70 | CH₃—C(CH₃)=CH—CH₂ | S | S | NH | S | S | |
| 71 | CH₃—C(CH₃)=CH—CH₂ | O | O | NH | S | S | |
| 72 | CH₃—CH₂—CH(CH₃) | S | S | O | S | S | 346 |

TABLE A-continued $$R-W^1-\underset{}{\underset{}{\bigcirc}}-W-CH_2-CH_2-X-\overset{Y}{\underset{\|}{C}}-X^1-CH_2CH_3$$

| Cpd | R | W¹ | W | X | Y | X¹ | m/s (M⁺) |
|---|---|---|---|---|---|---|---|
| 73 | CH₃—CH₂—CH(CH₃) | O | O | O | S | S | 314 |
| 74 | CH₃—C(CH₃)=CH—CH₂ | S | S | O | S | S | |
| 75 | CH₃—C(CH₃)=CH—CH₂ | O | O | O | S | S | |
| 76 | CH₃—CH₂—CH(CH₃) | O | S | NH | O | O | 297 |
| 77 | CH₃—C(CH₃)=CH—CH₂ | O | S | NH | O | O | |
| 78 | CH₂=C(F)—CH(CH₃) | O | O | NH | O | O | 297 |
| 79 | CH₃—CH=C(F)—CH₂ | O | O | NH | O | O | 297 |
| 80 | CH₃—CH₂—CH(CH₃) | S(=O) | O | NH | O | O | 314* |
| 81 | CH₃—CH₂—CH(CH₃) | O=S=O | O | NH | O | O | |
| 82 | CH₃—CH₂—CH(CH₃) | O | O | NCH₃ | O | O | 295.3 |
| 83 | CH₃—CH₂—CH(CH₃) | S | O | NH | O | S | 314* |
| 84 | CH₃—CH₂—CH(CH₃) | S | O | O | O | S | 314 |
| 85 | CH₃—CH₂—CH(CH₃) | S | O | O | S | S | 330 |
| 86 | CH₃—CH₂—CH(CH₃) | S | O | NH | S | S | 330 |
| 87 | CH₃—CH₂—CH(CH₃) | O | O | S | O | NH | 298 |
| 88 | CH₃—CH₂—CH(CH₃) | S | O | S | O | NH | 314 |

*M⁺ + H
**M⁺ + NH₄
M⁺ − HCl

TABLE B $$CH_3-CH_2-\underset{\underset{CH_3}{|}}{CH}-W^1-\underset{}{\underbrace{\bigcirc}}-W-\underset{\underset{R^2}{|}}{\overset{\overset{R^1}{|}}{CH}}-CH_2-X-\overset{\overset{Y}{\|}}{C}-X^1-R^7$$

| Cpd | W¹ | W | R¹ | X | Y | X¹ | R⁷ | m/s (M⁺) |
|---|---|---|---|---|---|---|---|---|
| 1 | O | O | CH₃ | NH | O | O | CH₂—CH₃ | 295 |
| 2 | O | O | H | NH | O | O | CH₃ | |
| 3 | O | O | H | NH | O | O | CH—(CH₃)₂ | 295 |
| 4 | O | O | H | NH | O | O | 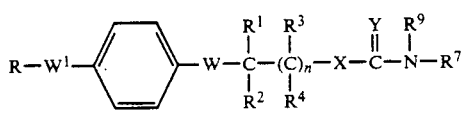 | |
| 5 | O | O | H | NH | O | O | CH₂—CH=CH₂ | |
| 6 | O | O | H | NH | O | O | CH₂—CH₂—CH₃ | 295 |
| 7 | O | O | H | O | O | NH | CH—(CH₃)₂ | 295 |
| 8 | O | O | H | O | O | NH | CH₂—CH₂—Cl | 315 |
| 9 | O | O | H | O | O | NH | C—(CH₃)₃ | 309 |
| 10 | O | O | H | O | O | NH | CH₂—CH₂=CH₂ | 293 |
| 11 | O | O | H | O | S | NH | CH₂—CH₂—CH₃ | 312 |
| 12 | O | O | H | O | S | NH | CH—(CH₃)₂ | 311 |
| 13 | O | O | CH₃ | O | O | NH | CH₂—CH₃ | 295 |
| 14 | S | O | H | O | O | NH | CH—(CH₃)₂ | 311 |
| 15 | S | O | CH₃ | O | O | NH | CH₂—CH₃ | 312 |
| 16 | S | O | CH₃ | O | S | NH | CH₂—CH₃ | 328 |
| 17 | O | O | H | O | O | N—CH₂CH₃ | CH₂—CH₃ | 309 |
| 18 | O | O | H | O | S | N—CH₃ | CH₃ | 297 |
| 19 | O | O | H | O | S | N—CH₂CH₃ | CH₂CH₃ | 325 |
| 20 | O | O | H | O | O | N—CH(CH₃)₂ | CH(CH₃)₂ | 338 |
| 21 | O | O | H | O | O | NH | CH(CH₃)—CH₂—CH₃ | 310 |
| 22 | O | O | H | O | O | NH | CH——CH₂ \ CH₂ / | 294* |
| 23 | O | O | H | NH | O | O | CH(CH₃)₂ | 295 |
| 24 | O | O | H | NH | O | S | CH(CH₃)₂ | 312 |
| 25 | O | O | H | NH | O | S | CH₂CH₃ | 298 |
| 26 | O | O | H | NH | O | O | CH(CH₃)—CH₂—CH₃ | 310* |
| 27 | O | O | CH₃ | NH | O | O | CH(CH₃)₂ | 309 |
| 28 | O | O | CH₃ | NH | O | S | CH(CH₃)₂ | 326 |
| 29 | O | O | CH₃ | NH | O | S | CH₂—CH₃ | 312 |
| 30 | O | O | CH₃ | NH | O | O | CH(CH₃)—CH₂—CH₃ | |
| 31 | S | O | CH₃ | NH | O | S | CH₂—CH₃ | 328 |
| 32 | S | O | CH₃ | NH | O | O | CH₂—CH₃ | 311 |
| 33 | O | O | H | NH | S | O | CH₂—CH₃ | 298 |
| 34 | C(=O) | O | H | NH | O | O | CH₂—CH₃ | 293 |
| 35 | NH | O | H | O | O | NH | CH₂—CH₃ | 280 |
| 36 | O | O | H | S | O | N—CH₃ | CH₃ | 298 |
| 37 | O | O | H | S | O | N—CH₃ | CH₂CH₃ | 312 |

*M⁻ + H

What is claimed is:

1. A compound of the following formula:

$$R-W^1-\underset{}{\underbrace{\bigcirc}}-W-\underset{\underset{R^2}{|}}{\overset{\overset{R^1}{|}}{C}}-\underset{\underset{R^4}{|}}{\overset{\overset{R^3}{|}}{(C)_n}}-X-\overset{\overset{Y}{\|}}{C}-\overset{\overset{R^9}{|}}{N}-R^7$$

wherein,
n is zero, one, two or three;
R is C₄-C₆ branched alkyl or alkenyl;
R⁷ is C₁₋₈ alkyl, optionally substituted with 1 to 6 halogen atoms; C₂₋₈-alkenyl, containing 1 or 2 ethylenic bonds and optionally substituted with 1 to 6 halogen atoms; or C₂₋₈ alkynyl, containing 1 or 2 acetylenic bonds and optionally substituted with 1 to 6 halogen atoms;
R⁹ is hydrogen or selected from the value of R⁷;
W is oxygen or sulfur;
W¹ is oxygen or sulfur;
X is oxygen or sulfur;
Y is oxygen or sulfur;

2. A compound according to claim 1 wherein W, W¹ and Y are oxygen, n is 1 and R², R³ and R⁴ are hydrogen.

3. A compound according to claim 2 wherein R¹ is hydrogen or methyl, R⁷ is lower alkyl of 1 to 4 carbon atoms and R⁹ is hydrogen or lower alkyl of 1 to 4 carbon atoms.

4. A compound according to claim 2 wherein R is 3-methylbutenyl or 1-methylpropyl.

5. A compound according to claim 3 wherein R is 3-methylbutenyl or 1-methylpropyl.

6. A compound according to claim 1 wherein X is oxygen.

7. A compound according to claim 2 wherein X is oxygen.

8. A compound according to claim 1 wherein W is oxygen.

9. A compound according to claim 8 wherein $R^7$ is lower alkyl of 1 to 4 carbon atoms and $R^9$ is hydrogen or lower alkyl of 1 to 4 carbon atoms.

10. A compound according to claim 9 wherein R is 3-methyl-2-butenyl or 1-methylpropyl.

11. A compound according to claim 1 selected from the group consisting of
O-2-[4-(1-methylpropoxy)phenoxy N-ethylcarbamate;
O-2-[4-(1-methylpropoxy)phenoxy N,N-diethylthiocarbamate;
O-2-[4-(3-methyl-2-butenoxy)phenoxy]ethyl N-isopropylcarbamate.

12. A compound according to claim 1 selected from the group consisting of
O-2-[4-(3-methyl-2-butenoxy)phenoxy]ethyl N-ethylcarbamate;
O-2-[4-(1-methylpropoxy)phenoxy]ethyl N-isopropylcarbamate;
O-2-[4-(1-methylpropoxy)phenoxy]ethyl N-t-butylcarbamate;
O-2-[4-(1-methylpropoxy)phenoxy]ethyl N,N-diethylcarbamate;
O-2-[4-(1-methylpropoxy)phenoxy]ethyl N-ethylthiocarbamate;
O-2-[4-(1-methylpropoxy)phenoxy]ethyl N-isopropylthiocarbamate;
O-2-[4-(1-methylpropylthio)phenoxy]ethyl N-ethylthiocarbamate;
O-2-[4-(1-methylpropylthio)phenoxy]ethyl N-isopropylcarbamate;
S-2-[4-(1-methylpropylthio)phenoxy]ethyl N-ethylthiocarbamate;
O-2-[4-(1-methylpropylthio)phenoxy]ethyl N-ethylthiocarbamate.

13. A compound according to claim 1 selected from the group consisting of
O-2-[(R)-4-(1-methylpropoxy]ethyl N-ethylcarbamate;
O-2-[(S)-4-(1-methylpropoxy]ethyl N-ethylcarbamate.

* * * * *